United States Patent
Kushwah et al.

(10) Patent No.: US 11,670,323 B2
(45) Date of Patent: Jun. 6, 2023

(54) SYSTEMS AND METHODS FOR DETECTING IMPAIRMENT OF AN INDIVIDUAL

(71) Applicant: PredictMedix Inc., Toronto (CA)

(72) Inventors: Rahul Kushwah, Toronto (CA); Sheldon Kales, Toronto (CA); Nandan Mishra, Noida (IN); Himanshu Ujjawal Singh, Malviya Nagar (IN); Saurabh Gupta, Jalaun (IN)

(73) Assignee: PredictMedix Inc., Toronto (CA)

( * ) Notice: Subject to any disclaimer, the term of this patent is extended or adjusted under 35 U.S.C. 154(b) by 191 days.

(21) Appl. No.: 16/892,369

(22) Filed: Jun. 4, 2020

(65) Prior Publication Data

US 2020/0387696 A1 Dec. 10, 2020

Related U.S. Application Data

(60) Provisional application No. 62/858,422, filed on Jun. 7, 2019.

(51) Int. Cl.
   *G06V 40/20* (2022.01)
   *G06T 7/00* (2017.01)
   *G10L 25/48* (2013.01)

(52) U.S. Cl.
   CPC ............ *G06V 40/20* (2022.01); *G06T 7/0002* (2013.01); *G06T 7/97* (2017.01); *G10L 25/48* (2013.01)

(58) Field of Classification Search
   None
   See application file for complete search history.

(56) References Cited

U.S. PATENT DOCUMENTS

| | | | |
|---|---|---|---|
| 7,027,621 B1 | 4/2006 | Prokoski | |
| 9,135,803 B1 | 9/2015 | Fields et al. | |
| 9,775,512 B1* | 10/2017 | Tyler | G06V 20/64 |
| 2007/0124135 A1* | 5/2007 | Schultz | G10L 17/26 |
| | | | 704/201 |
| 2015/0314681 A1* | 11/2015 | Riley, Sr. | B60K 28/066 |
| | | | 340/576 |
| 2017/0000344 A1* | 1/2017 | Visconti | G06V 40/193 |
| 2017/0049362 A1* | 2/2017 | Macknik | A61B 5/4845 |
| 2017/0162197 A1* | 6/2017 | Cohen | G10L 15/22 |
| 2020/0121235 A1* | 4/2020 | Gibbons | G16H 50/20 |
| 2020/0390337 A1* | 12/2020 | Frank | G01J 5/0265 |
| 2021/0264395 A1* | 8/2021 | Trelin | G06Q 20/206 |

* cited by examiner

*Primary Examiner* — Leon Viet Q Nguyen

(57) ABSTRACT

System and methods are provided for detecting impairment of an individual. The method involves operating a processor to: receive at least one image associated with the individual; and identify at least one feature in each image. The method further involves operating the processor to, for each feature: generate an intensity representation for that feature; apply at least one impairment analytical model to the intensity representation to determine a respective impairment likelihood; and determine a confidence level for each impairment likelihood based on characteristics associated with at least the applied impairment analytical model and that feature. The method further involves operating the processor to: define the impairment of the individual based on at least one impairment likelihood and the respective confidence level.

14 Claims, 9 Drawing Sheets

SYSTEMS AND METHODS FOR DETECTING IMPAIRMENT OF AN INDIVIDUAL

CROSS-REFERENCE TO RELATED PATENT APPLICATIONS

This application claims the benefit of U.S. Provisional Application No. 62/858,422, filed on Jun. 7, 2019. The complete disclosure of U.S. Provisional Application No. 62/858,422, is incorporated herein by reference.

FIELD

The described embodiments relate to systems and methods for detecting impairment of an individual.

BACKGROUND

When an individual is under the influence of an impairing substance, that individual can be unable to safely perform certain tasks. For example, the use of drugs, such as *cannabis*, or alcohol can impair an individual's physiological and/or psychological state. When the task to be performed requires the individual to be alert and/or focused, impairment can lead to significant safety risks. For example, an impaired individual operating a vehicle (or other heavy machinery) can lose control of the vehicle and cause harm to himself or herself and nearby individuals and property. Detection of impairment in individuals, therefore, can mitigate, or possibly even prevent, any accidents resulting from actions of impaired individuals.

SUMMARY

The various embodiments described herein generally relate to methods (and associated systems configured to implement the methods) for detecting impairment of an individual.

In accordance with some embodiments, there is provided a method for detecting impairment of an individual. The method involves operating a processor to: receive at least one image associated with the individual; and identify at least one feature in each image. The method further involves operating the processor to, for each feature: generate an intensity representation for that feature; apply at least one impairment analytical model to the intensity representation to determine a respective impairment likelihood; and determine a confidence level for each impairment likelihood based on characteristics associated with at least the applied impairment analytical model and that feature. The method further involves operating the processor to: define the impairment of the individual based on at least one impairment likelihood and the respective confidence level.

In some embodiments, determining the confidence level for each impairment likelihood based on the characteristics associated with at least the applied impairment analytical model and the feature involves: determining whether an image quality of the at least one image satisfies a quality threshold; generating a quality indicator according to whether the image quality satisfies the quality threshold; and determining the confidence level for each impairment likelihood based at least on the quality indicator.

In some embodiments, determining the confidence level for each impairment likelihood based on the characteristics associated with at least the applied impairment analytical model and the feature involves: determining an image reliability indicator associated with an image view of the at least one image; and determining the confidence level for each impairment likelihood based at least on the image reliability indicator.

In some embodiments, determining the confidence level for each impairment likelihood based on the characteristics associated with at least the applied impairment analytical model and the feature involves: determining a feature reliability indicator associated with the feature; and determining the confidence level for each impairment likelihood based at least on the feature reliability indicator.

In some embodiments, determining the confidence level for each impairment likelihood based on the characteristics associated with at least the applied impairment analytical model and the feature involves: determining a model reliability indicator associated with the impairment analytical model; and determining the confidence level for each impairment likelihood based at least on the model reliability indicator.

In some embodiments, the method further involves operating the processor to: receive at least one audio recording involving the individual; identify at least one audio property of the at least one audio recording to analyze. The method further involves operating the processor to, for each audio property: select at least one audio analytical model for that audio property; apply the at least one audio analytical model to the at least one audio recording to determine a respective impairment likelihood of the individual; and determine the confidence level for each impairment likelihood based on characteristics associated with at least the applied audio analytical model and that audio property.

In some embodiments, identifying the at least one audio property involves identifying at least one of loudness, jitteriness, and/or pitch.

In some embodiments, defining the impairment of the individual involves generating a weighted average based on each impairment likelihood and the respective confidence levels.

In some embodiments, defining the impairment of the individual involves: determining whether the respective confidence level satisfies a confidence threshold; and eliminating one or more impairment likelihoods associated with the confidence level below the confidence threshold.

In some embodiments, defining the impairment of the individual involves generating an impairment indicator indicating an impairment level of the individual.

In some embodiments, defining the impairment of the individual involves:

determining whether the at least one impairment likelihood and the respective confidence level satisfies an impairment threshold; and generating the impairment indicator as impaired when the at least one impairment likelihood and the respective confidence level satisfy the impairment threshold, otherwise, generating the impairment indicator as acceptable.

In some embodiments, the method further involves operating the processor to: determine whether the at least one impairment likelihood and the respective confidence level satisfy a first impairment threshold; in response to determining the at least one impairment likelihood and the respective confidence level satisfy the first impairment threshold, generate the impairment indicator as impaired; in response to determining the at least one impairment likelihood and the respective confidence level do not satisfy the first impairment threshold, determine whether the at least one impairment likelihood and the respective confidence level satisfies a second impairment threshold lower than the first impairment threshold; and in response to determining the at least one impairment likelihood and the respective confidence level satisfy the second impairment threshold, generate the impairment indicator as likely impaired, otherwise, generate the impairment indicator as acceptable.

In some embodiments, defining the impairment of the individual involves generating the impairment indicator to indicate the impairment level of the individual by *cannabis*.

In some embodiments, generating the intensity representation for the feature involves generating a histogram to represent intensity values of imaging data associated with the feature.

In some embodiments, identifying the at least one feature in each image involves: applying at least one feature analytical model to the image data to identify the at least one feature depicted by the image data.

In some embodiments, the method further involves operating the processor to: receive a set of feature training images associated with a plurality of individuals; associate each feature training image with one or more features; and generate a feature analytical model based on the set of feature training images and the feature associated with each feature training image.

In some embodiments, generating the feature analytical model involves applying a pattern recognition algorithm to the set of feature training images and the feature associated with each feature training image.

In some embodiments, the method further involves extracting a portion of the image data from which to identify the at least one feature in each image.

In some embodiments, generating the intensity representation for that feature involves generating the intensity representation for the extracted portion of image data.

In some embodiments, extracting the portion of the image data depicting the at least one portion of the individual involves applying at least one of a technique based on histograms of gradient, Haar-like features, local binary patterns, and/or Haralick features.

In some embodiments, identifying the at least one feature in each image involves: preprocessing the at least one image to at least improve image data quality of the at least one image.

In some embodiments, receiving the at least one image associated with the individual involves receiving two or more images associated with the individual.

In some embodiments, defining the impairment of the individual involves generating an impairment indicator indicating an impairment level of the individual based on the at least one impairment likelihood and the respective confidence level associated with each image of the two or more images.

In some embodiments, receiving the at least one image associated with the individual involves receiving an image depicting at least a portion of a body of the individual.

In some embodiments, receiving the at least one image associated with the individual involves receiving: a first image depicting a first portion of the individual; and a second image depicting a second portion of the individual, the second portion of the individual being different from the first portion of the individual.

In some embodiments, receiving the at least one image associated with the individual involves receiving: a first image depicting a first view of a portion of the individual; and a second image depicting a second view of the portion of the individual, the second view being different from the first view.

In some embodiments, receiving the at least one image associated with the individual involves receiving at least one infrared image associated with the individual.

In some embodiments, the method further involves operating the processor to: receive a set of impairment training images associated with a plurality of individuals; associate each impairment training image with an impairment level; and generate an impairment analytical model based on the set of impairment training images and the impairment level associated with each impairment training image.

In some embodiments, generating the impairment analytical model involves applying a pattern recognition algorithm to the set of impairment training images and the one or more associated impairment levels.

In some embodiments, the pattern recognition algorithm includes an algorithm based on at least one of Nearest Neighbor, K-Nearest Neighbors, Support Vector Machines, Naive Bayesian, Decision Trees, Random Forests, Logistic Regression, and/or Linear Discriminant Analysis.

In accordance with some embodiments, there is provided a non-transitory computer-readable medium including instructions executable on a processor for implementing the method.

In accordance with some embodiments, there is provided a system for detecting impairment of an individual. The system includes a data storage and a processor. The data storage can store at least one impairment analytical model. The processor is operable to: receive, via a network, at least one image associated with the individual; and identify at least one feature in each image. The processor is further operable to, for each feature: generate an intensity representation for that feature; apply the at least one impairment analytical model stored in the memory to the intensity representation to determine a respective impairment likelihood; and determine a confidence level for each impairment likelihood based on characteristics associated with at least the applied impairment analytical model and that feature. The processor is further operable to: define the impairment of the individual based on at least one impairment likelihood and the respective confidence level.

In some embodiments, the processor is operable to: determine whether an image quality of the at least one image satisfies a quality threshold; generate a quality indicator according to whether the image quality satisfies the quality threshold; and determine the confidence level for each impairment likelihood based at least on the quality indicator.

In some embodiments, the processor is operable to: determine an image reliability indicator associated with an image view of the at least one image; and determine the confidence level for each impairment likelihood based at least on the image reliability indicator.

In some embodiments, the processor is operable to: determine a feature reliability indicator associated with the feature; and determine the confidence level for each impairment likelihood based at least on the feature reliability indicator.

In some embodiments, the processor is operable to: determine a model reliability indicator associated with the impairment analytical model; and determine the confidence level for each impairment likelihood based at least on the model reliability indicator.

In some embodiments, the processor is operable to: receive at least one audio recording involving the individual; and identify at least one audio property of the at least one audio recording to analyze. The processor is further operable to, for each audio property: select at least one audio analytical model for that audio property; apply the at least one audio analytical model to the at least one audio recording to determine a respective impairment likelihood of the individual; and determine the confidence level for each impairment likelihood based on characteristics associated with at least the applied audio analytical model and that audio property.

In some embodiments, the at least one audio property is selected from at least one of loudness, jitteriness, and/or pitch.

In some embodiments, the processor is operable to generate a weighted average based on each impairment likelihood and the respective confidence levels.

In some embodiments, the processor is operable to: determine whether the respective confidence level satisfies a confidence threshold; and eliminate one or more impairment likelihoods associated with the confidence level below the confidence threshold.

In some embodiments, the processor is operable to generate an impairment indicator indicating an impairment level of the individual.

In some embodiments, the processor is operable to: determine whether the at least one impairment likelihood and the respective confidence level satisfies an impairment threshold; and generate the impairment indicator as impaired when the at least one impairment likelihood and the respective confidence level satisfy the impairment threshold, otherwise, generating the impairment indicator as acceptable.

In some embodiments, the processor is operable to: determine whether the at least one impairment likelihood and the respective confidence level satisfy a first impairment threshold; in response to determining the at least one impairment likelihood and the respective confidence level satisfy the first impairment threshold, generate the impairment indicator as impaired; in response to determining the at least one impairment likelihood and the respective confidence level do not satisfy the first impairment threshold, determine whether the at least one impairment likelihood and the respective confidence level satisfies a second impairment threshold lower than the first impairment threshold; and in response to determining the at least one impairment likelihood and the respective confidence level satisfy the second impairment threshold, generate the impairment indicator as likely impaired, otherwise, generate the impairment indicator as acceptable.

In some embodiments, the processor is operable to generate the impairment indicator to indicate the impairment level of the individual by *cannabis*.

In some embodiments, the processor is operable to generate a histogram to represent intensity values of imaging data associated with the feature.

In some embodiments, the processor is operable to: apply at least one feature analytical model to the image data to identify the at least one feature depicted by the image data.

In some embodiments, the processor is operable to: receive a set of feature training images associated with a plurality of individuals; associate each feature training image with one or more features; and generate a feature analytical model based on the set of feature training images and the one or more features associated with each feature training image.

In some embodiments, the processor is operable to apply a pattern recognition algorithm to the set of feature training images and the one or more features associated with each feature training image to generate the feature analytical model.

In some embodiments, the processor is operable to extract a portion of the image data from which to identify the at least one feature in each image.

In some embodiments, the processor is operable to generate the intensity representation for the extracted portion of image data.

In some embodiments, the processor is operable to apply at least one of a technique based on histograms of gradient, Haar-like features, local binary patterns, and/or Haralick features.

In some embodiments, the processor is operable to: preprocess the at least one image to at least improve image data quality of the at least one image.

In some embodiments, the processor is operable to receive two or more images associated with the individual.

In some embodiments, the processor is operable to generate an impairment indicator indicating an impairment level of the individual based on the at least one impairment likelihood and the respective confidence level associated with each image of the two or more images.

In some embodiments, the processor is operable to receive an image depicting at least a portion of a body of the individual.

In some embodiments, the processor is operable to receive: a first image depicting a first portion of the individual; and a second image depicting a second portion of the individual, the second portion of the individual being different from the first portion of the individual.

In some embodiments, wherein the processor is operable to receive: a first image depicting a first view of a portion of the individual; and a second image depicting a second view of the portion of the individual, the second view being different from the first view.

In some embodiments, the processor is operable to receive at least one infrared image associated with the individual.

In some embodiments, the processor is operable to: receive a set of impairment training images associated with a plurality of individuals; associate each impairment training image with an impairment indicator indicating an impairment level of an individual associated with that impairment training image; generate an impairment analytical model based on the set of impairment training images and the impairment indicator associated with each impairment training image.

In some embodiments, generating the impairment analytical model involves applying a pattern recognition algorithm to the set of impairment training images and the impairment level associated with each impairment training image.

In some embodiments, pattern recognition algorithm includes an algorithm based on at least one of Nearest Neighbor, K-Nearest Neighbors, Support Vector Machines, Naive Bayesian, Decision Trees, Random Forests, Logistic Regression, and/or Linear Discriminant Analysis.

In accordance with some embodiments, there is provided a method for detecting impairment of an individual. The method involves operating a processor to: receive at least one dataset associated with one or more features related to the individual. The method further involves operating the processor to, for each feature: apply at least one impairment analytical model to the at least one dataset to determine a respective impairment likelihood; and determine a confidence level for each impairment likelihood based on characteristics associated with at least the applied impairment analytical model and that feature. The method further involves operating the processor to: define the impairment of the individual based on at least one impairment likelihood and the respective confidence level.

In some embodiments, receiving the at least one dataset associated with the one or more features related to the individual involves receiving at least one of an image associated with the individual, an audio recording associated with the individual, a brain wave recording associated with the individual, a heart rate measurement associated with the individual, a hydration level associated with the individual, and/or an electrocardiogram (ECG) recording associated with the individual.

In some embodiments, the method further involves operating the processor to: receive a set of training data related to each feature; associate each training data with an impairment likelihood; and generate an impairment analytical model based on the set of training data and the impairment likelihood associated with each training data.

In accordance with some embodiments, there is provided a non-transitory computer-readable medium including instructions executable on a processor for implementing the method.

In accordance with some embodiments, there is provided a system for detecting impairment of an individual. The system includes a data storage and a processor. The data storage can store at least one impairment analytical model. The processor is operable to: receive, via a network, at least one dataset associated one or more features related to the individual. The processor is further operable to, for each feature: apply at least one impairment analytical model to the at least one dataset to determine a respective impairment likelihood; and determine a confidence level for each impairment likelihood based on characteristics associated with at least the applied impairment analytical model and that feature. The processor is further operable to: define the impairment of the individual based on at least one impairment likelihood and the respective confidence level.

In some embodiments, the processor is operable to receive at least one of an image associated with the individual, an audio recording associated with the individual, a brain wave recording associated with the individual, a heart rate recording associated with the individual, a hydration recording associated with the individual, and/or an electrocardiogram (ECG) recording associated with the individual.

In some embodiments, the processor is operable to: receive a set of training data related to each feature; associate each training data with an impairment likelihood; and generate an impairment analytical model based on the set of training data and the impairment likelihood associated with each training data.

BRIEF DESCRIPTION OF THE DRAWINGS

Several embodiments will now be described in detail with reference to the drawings, in which.

Figure 1:
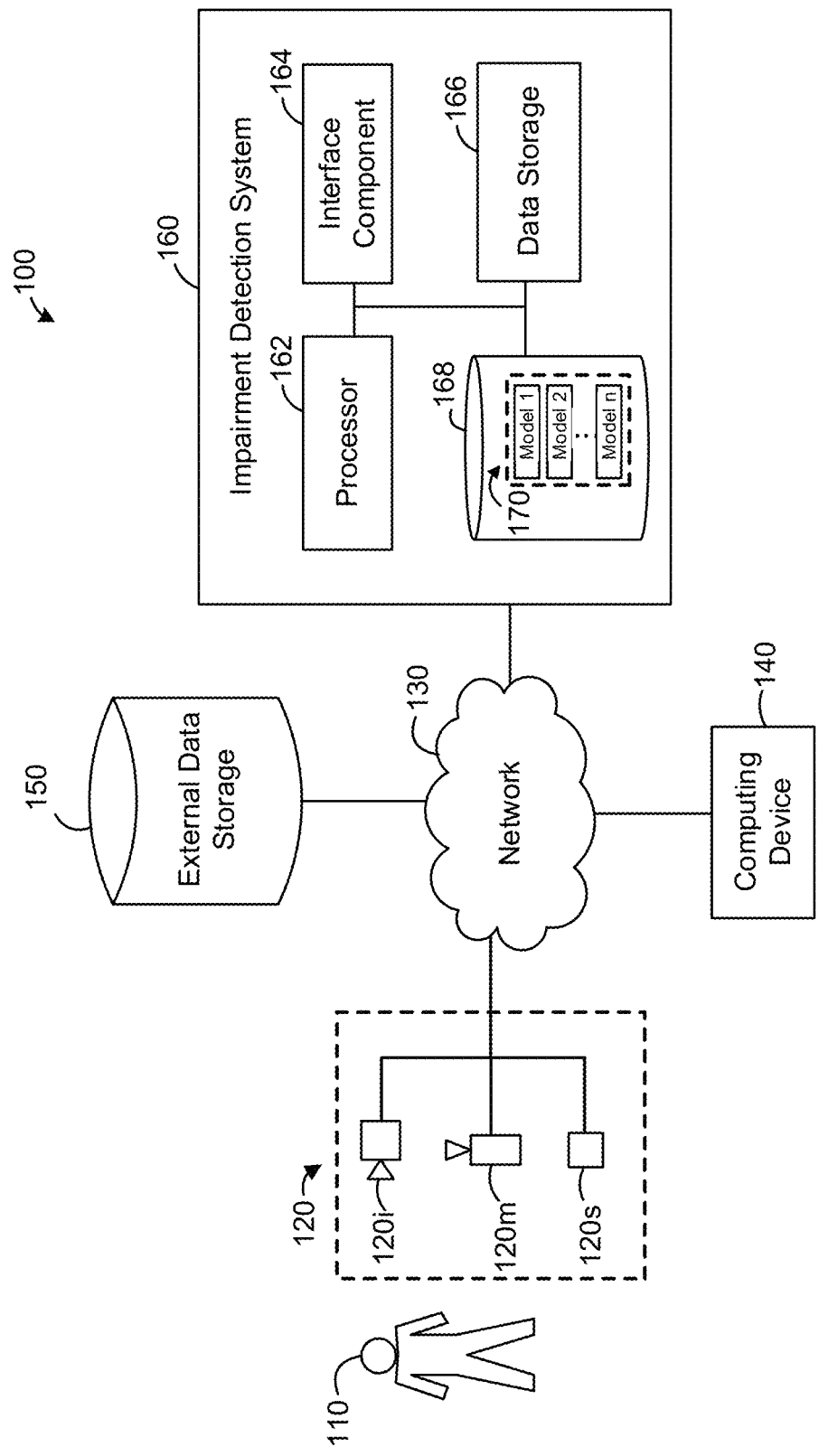
FIG. 1 is a block diagram of components interacting with an impairment detection system, in accordance with an example embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

When an individual is under the influence of an impairing substance, that individual is likely to have trouble focusing and staying alert. As a result, it can be harmful to that individual, and nearby individuals and property, for that individual to undertake tasks that typically involve some level of physical skill and judgment, such as, but not limited to, operating tools and machines (e.g., motor vehicle, boat, etc.), childcare, hunting, recreational activities that are high-speed and/or in potentially hazardous terrain (e.g., skiing, biking, mountain climbing, etc.), and activities involving potentially hazardous materials and/or environments (e.g., mining, emergency response, etc.). Example impairing substances can include alcohol and drugs, such as *cannabis*.

With alcohol, blood alcohol concentration (BAC) is primarily used as a measurement of intoxication. An individual's blood alcohol concentration after consuming alcohol can depend on various factors, such as, but not limited to, the ingredients of the beverage, rate of alcohol consumption, and the individual's personal characteristics (e.g., age, gender, body type, metabolism, emotional state, alcohol tolerance, etc.). Without undergoing a blood test at a time proximal to consuming the alcohol, it can be difficult to accurately estimate one's blood alcohol concentration. An often used instrument to measure blood alcohol concentration is the breathalyzer. Although convenient, the breathalyzer has limitations. Before using the breathalyzer, it is important to properly calibrate the instrument to obtain an accurate estimate. The timing at which the breathalyzer is used following consumption of food and/or alcohol can also affect the measurement.

Impairment resulting from use of *cannabis* is a growing concern. Medical and recreational use of *cannabis* has been recently decriminalized or legalized in many countries. In Canada, *cannabis* for recreational use was legalized in 2018, while medical use has been legal since 2001. In the United States, although currently illegal at the federal level, medical and recreation use has been legalized in numerous states. This recent legalization and decriminalization of recreational *cannabis* has led to an increasing awareness of the effects that *cannabis* can have on the motor skills and mental judgment of individuals—in particular, when they are operating heavy machineries, such as motor vehicles.

Impairment resulting from *cannabis* use can be difficult to detect. In contrast to alcohol impairment, there is no similar instrument for detecting *cannabis* use. The concentration of *cannabis* (and its psychoactive constituents) present within an individual who recently used *cannabis* is typically very low. Also, this concentration cannot easily be correlated to an impairment level.

The various embodiments described herein generally relate to methods (and associated systems configured to implement the methods) for detecting impairment of an individual. The impairment can result from various impairing substances, such as, but not limited to, alcohol and drugs. The disclosed methods and systems apply analytical models that are generated based on sets of training data. The sets of training data contain example data that are known to satisfy specific parameters. Unlike traditional methods which rely on explicit programming, the disclosed systems generate the analytical models by determining patterns within each set of training data and making inferences from each set of training data.

The impairment detection systems disclosed herein can provide an efficient and reasonably accurate determination of impairment of an individual. As will be described, the impairment detection systems disclosed herein can analyze a wide variety of different types of data and different properties of the different types of data. The impairment detection systems can, in some embodiments, define the impairment of an individual based on multiple different types of data and/or different properties. The impairment detection systems disclosed herein can be applied in various settings in which an individual needs to undertake tasks that typically involve some level of physical skill and judgment, such as, but not limited to, operating tools and machinery (e.g., motor vehicle, boat, etc.), childcare, hunting, recreational activities that are high-speed and/or in potentially hazardous terrain (e.g., skiing, biking, mountain climbing, etc.), and activities involving potentially hazardous materials and/or environments (e.g., mining, emergency response, etc.).

Reference is first made to FIG. 1, which illustrates a block diagram 100 of components interacting with an example impairment detection system 160. The impairment detection system 160 includes a processor 162, an interface component 164, and a data storage 166.

As shown in FIG. 1, the impairment detection system 160 can be in communication with an external data storage 150 and a computing device 140 via a network 130. The impairment detection system 160 can also be in communication with one or more sensing devices 120 via the network 130.

Although the impairment detection system 160 is shown as one component in FIG. 1, in some embodiments, the impairment detection system 160 can be provided with one or more servers distributed over a wide geographic area and connected via the network 130.

In FIG. 1, it is shown that the impairment detection system includes an analytical model database 168 with multiple analytical models 170 stored thereon. In some embodiments, the analytical model database 168 can be stored in the data storage 166 and/or in the external data storage 150 accessible via the network 130.

The processor 162 may be any suitable processor, controller or digital signal processor that provides sufficient processing power depending on the configuration, purposes and requirements of the impairment detection system 160. In some embodiments, the processor 162 can include more than one processor with each processor being configured to perform different dedicated tasks. The processor 162 controls the operation of the impairment detection system 160. For example, the processor 162 can receive a set of data associated with an individual 110 from a sensing device 120 and determine, in accordance with the methods disclosed herein, from the set of data whether the individual 110 is impaired.

The interface component 164 may be any interface that enables the impairment detection system 160 to communicate with other devices and systems. In some embodiments, the interface component 164 can include at least one of a serial port, a parallel port or a USB port. The interface component 164 may also include at least one of an Internet, Local Area Network (LAN), Ethernet, Firewire, modem or digital subscriber line connection. Various combinations of these elements may be incorporated within the interface component 164.

For example, the interface component 164 may receive input from various input devices, such as a mouse, a keyboard, a touch screen, a thumbwheel, a track-pad, a track-ball, a card-reader, voice recognition software and the like depending on the requirements and implementation of the impairment detection system 160.

The data storage 166 can include RAM, ROM, one or more hard drives, one or more flash drives or some other suitable data storage elements such as disk drives, etc. For example, the data storage 166 can include a memory on which one or more databases or file system(s) are stored. The database(s) can store information related to determining impairment an individual, such as, but not limited to, training data sets, datasets associated with individuals (e.g., images, audio clips, etc.) and analytical models related to those datasets. For example, the data storage 166 can store the analytical model database 168.

Similar to the data storage 166, the external data storage 150 can include RAM, ROM, one or more hard drives, one or more flash drives or some other suitable data storage elements such as disk drives, etc. The external data storage 150 can include a memory on which one or more databases or file system(s) are stored. Although only one external data storage 150 is shown, there may be multiple external data storages 150 distributed over a wide geographic area and connected via the network 130.

The external data storage 150 can be accessed by the impairment detection system 160 via the network 130. The external data storage 150 can act as a back-up data storage to the data storage 166 and/or store at least some of the data related to determining impairment of an individual. In some embodiments, the external data storage 150 can store data that is not as frequently used by the impairment detection system 160, or larger size data.

Each of the processor 162, the interface component 164, and the data storage 166 may be combined into a fewer number of components or may be separated into further components. The processor 162, the interface component 164, and the data storage 166 may be implemented in software or hardware, or a combination of software and hardware.

The computing device 140 may be any networked device operable to connect to the network 130. A networked device is a device capable of communicating with other devices through a network such as the network 130. A networked device may couple to the network 130 through a wired or wireless connection.

Although only one computing device 140 is shown in FIG. 1, there may be multiple computing devices 140 in communication with the impairment detection system 160 via the network 130. The computing devices 140 can be distributed over a wide geographic area. For example, a user can use a computing device 140 to access the impairment detection system 160 to determine impairment of an individual.

The computing devices 140 may include at least a processor and memory, and may be an electronic tablet device, a personal computer, workstation, server, portable computer, mobile device, personal digital assistant, laptop, smart phone, WAP phone, an interactive television, video display terminals, gaming consoles, and portable electronic devices or any combination of these. In some embodiments, the computing device 140 may be a laptop or a smartphone device equipped with a network adapter for connecting to the Internet.

In FIG. 1, example sensing devices 120, an image sensing device 120$i$, an audio sensing device 120$m$, and a heart rate monitor 120$s$, are shown. The illustrated sensing devices 120$i$, 120$m$, 120$s$ are only for illustration purposes and not intended to be limiting. Fewer or more sensing devices 120 can be included, in some embodiments. Alternative sensing devices 120 can also be included. The sensing devices 120 can be also be distributed over a wide geographic area.

The sensing devices 120 can include any device operable to collect data related to specific characteristics of an individual 110. For example, the image sensing device 120$i$ can capture images of the individual, the audio sensing device 120$m$ can capture audio recordings of the individual, and the heart rate monitor 120$s$ can monitor the heart rate of the individual. Other sensing devices 120 can be used to collect video recordings, brain wave recordings, data related to hydration levels, and/or electrocardiogram (ECG) recordings. It is possible that one sensing device 120 can capture more than one type of data.

The sensing devices 120 can communicate with the external data storage 150, the impairment detection system 160, and the computing device 140 via the network 130. For example, the impairment detection system 160 can receive sets of data collected by the sensing devices 120 via the network 130. In some embodiments, the sensing devices 120 can be a part of the computing device 140. The sensing devices 120 may include a processor and a memory.

For ease of exposition, only one individual 110 is shown. In some embodiments, the impairment detection system 160 can operate the sensing devices 120 to collect data from multiple individuals 110 located within the operating region of the sensing devices 120.

In some embodiments, the sensing devices 120 can be installed at a machine requiring some level of human operation. The machinery can include, but not limited to, motor vehicles (e.g., automobiles, trucks, etc.), boats, ships, airplanes, and heavy-duty vehicles. Before the individual 110 can operate the machine, the impairment detection system 160 can detect whether the individual 110 is impaired and only allow the individual 110 to proceed with operating the machine when the impairment detection system 160 determines that the individual 110 is not impaired.

The impairment detection system 160 can be installed at the machine, in part or in whole. For example, the sensing devices 120 can be installed at the machine and transmit collected data via the network 130 to a remote impairment detection system 160. In another example, the sensing devices 120 and some portion of the impairment detection system 160 can be installed at the machine, such as a sensor processor for receiving and conducting an initial processing of the collected data, and/or a data storage for initially storing the collected data for later transmission to the other remote components of the impairment detection system 160. In another example, the sensing devices 120 and the impairment detection system 160 can be installed at the machine.

Figure 2:
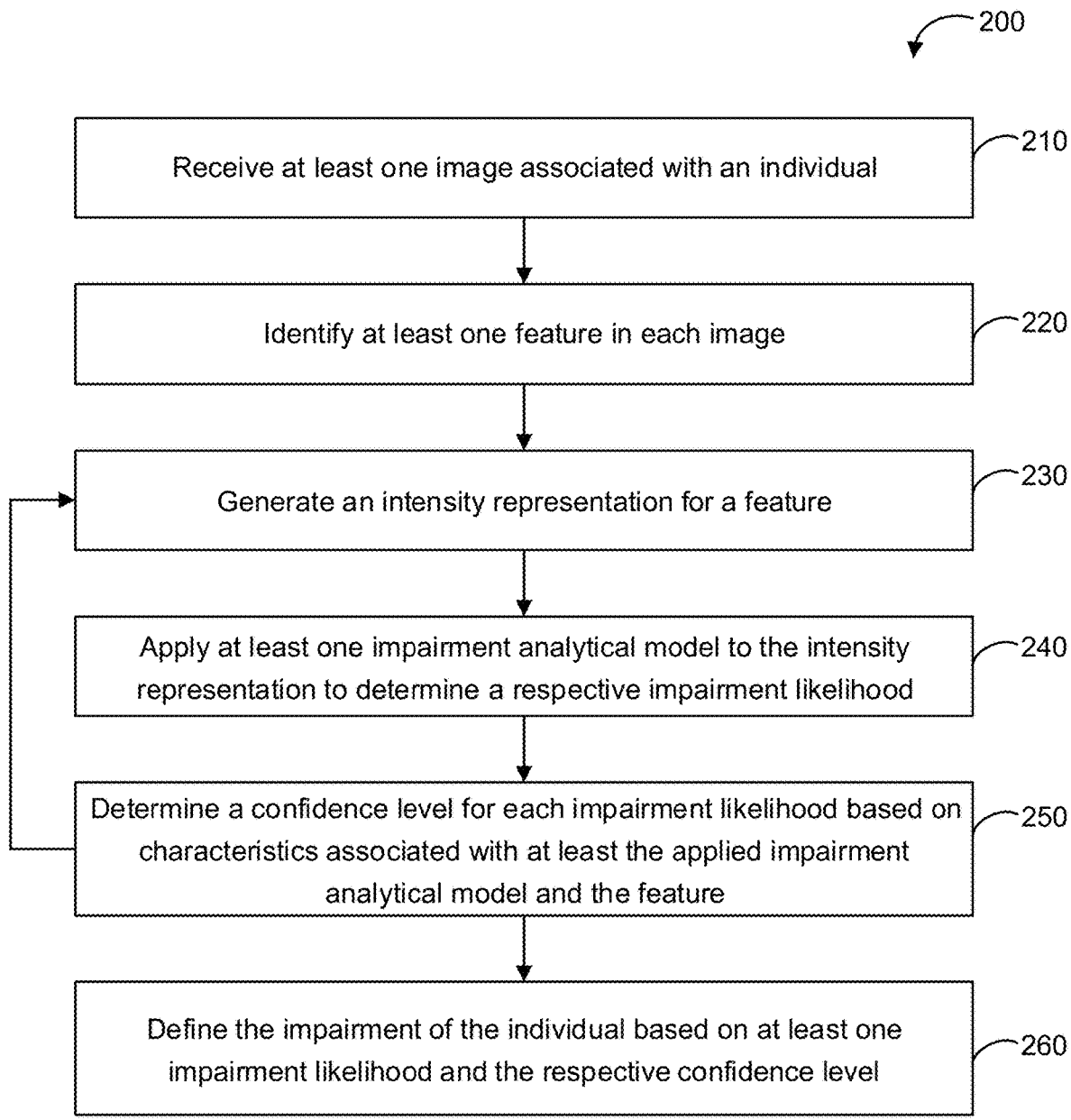
FIG. 2 is a flowchart of an example method of operating the impairment detection system for detecting impairment of the individual.
Figure 3A:
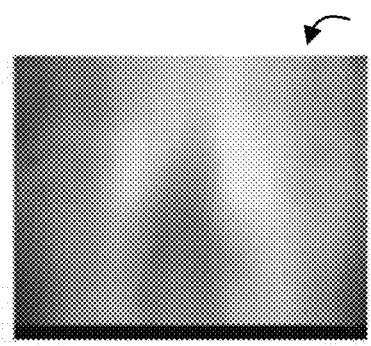
FIG. 3A is an infrared image of an individual's eyes and nose when the individual is under no impairment, in accordance with an example embodiment.
Figure 3B:
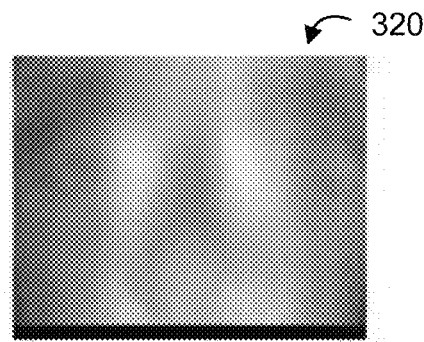
FIG. 3B shows the individual's eyes and nose in FIG. 3A when the individual is under impairment, in accordance with an example embodiment.
Figure 3C:
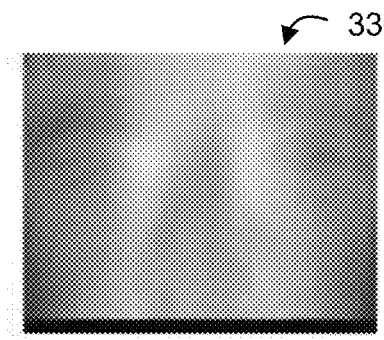
FIG. 3C shows the individual's eyes and nose in FIGS. 3A and 3B when the individual is at another impairment level, in accordance with an example embodiment.
Figure 3D:
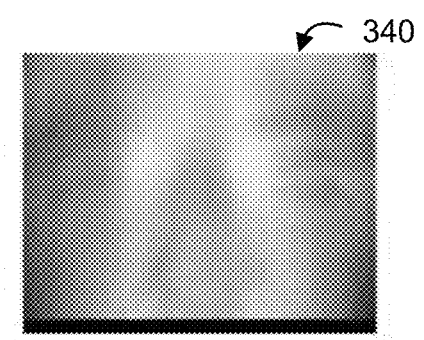
FIG. 3D shows the individual's eyes and nose in FIGS. 3A to 3C when the individual is at another impairment level, in accordance with an example embodiment.
Figure 4A:
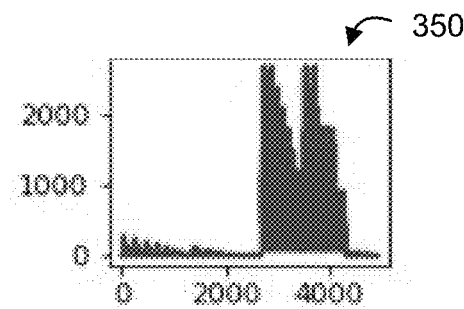
FIG. 4A is an example intensity representation corresponding to the infrared image in FIG. 3A, in accordance with at example embodiment.
Figure 4B:
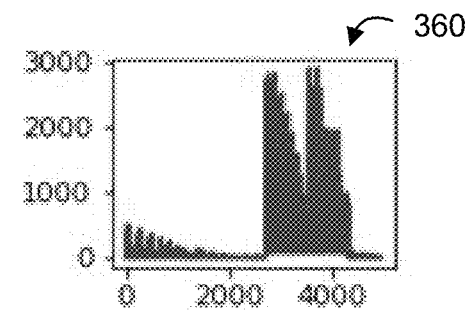
FIG. 4B is an example intensity representation corresponding to the infrared image in FIG. 3B, in accordance with at example embodiment.
Figure 4C:
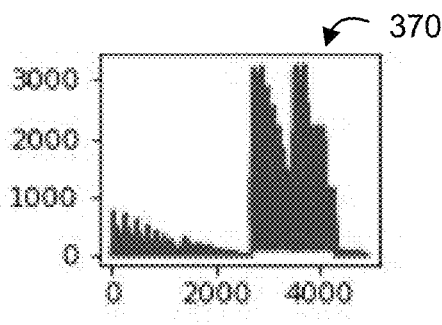
FIG. 4C is an example intensity representation corresponding to the infrared image in FIG. 3C, in accordance with at example embodiment.
Figure 4D:
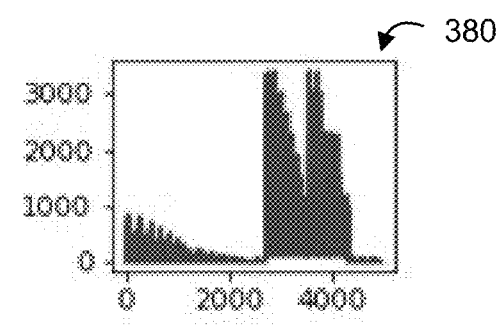
FIG. 4D is an example intensity representation corresponding to the infrared image in FIG. 3D, in accordance with at example embodiment.
Figure 5A:
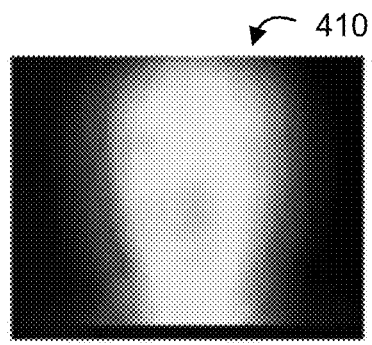
FIG. 5A is an infrared image of an individual's head when the individual is under no impairment, in accordance with an example embodiment.
Figure 5B:
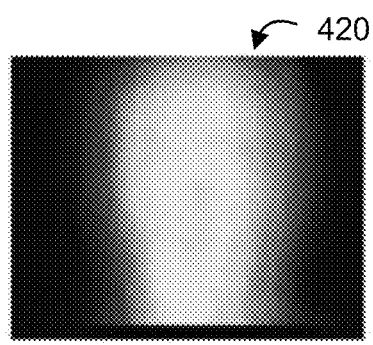
FIG. 5B shows the individual's head in FIG. 5A when the individual is under impairment, in accordance with an example embodiment.
Figure 5C:
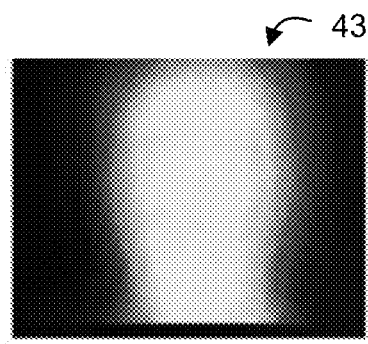
FIG. 5C shows the individual's head in FIGS. 5A and 5B when the individual is at another impairment level, in accordance with an example embodiment.
Figure 5D:
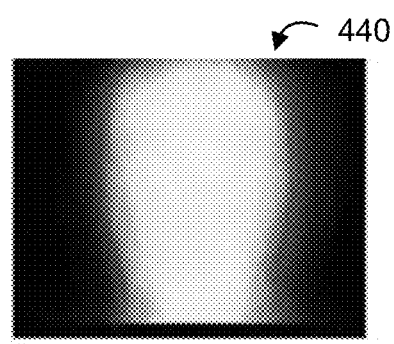
FIG. 5D shows the individual's head in FIGS. 5A to 5C when the individual is at another impairment level, in accordance with an example embodiment.
Figure 6A:
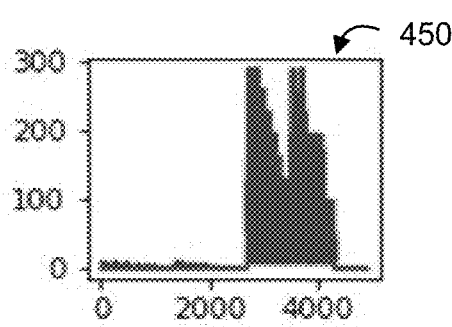
FIG. 6A is an example intensity representation corresponding to the infrared image in FIG. 5A, in accordance with at example embodiment.
Figure 6B:
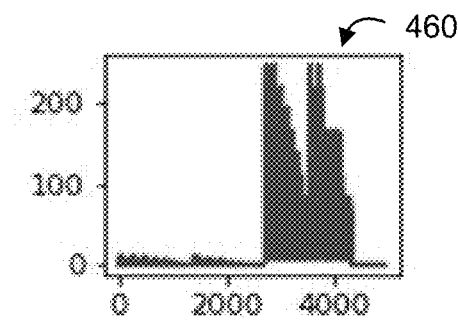
FIG. 6B is an example intensity representation corresponding to the infrared image in FIG. 5B, in accordance with at example embodiment.
Figure 6C:
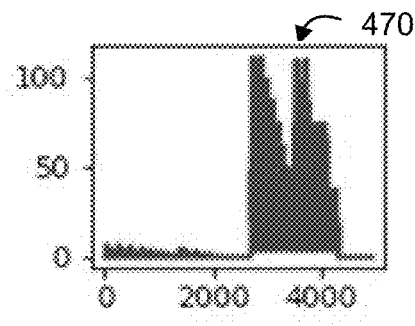
FIG. 6C is an example intensity representation corresponding to the infrared image in FIG. 5C, in accordance with at example embodiment.
Figure 6D:
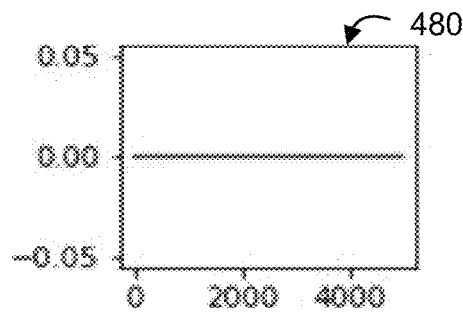
FIG. 6D is an example intensity representation corresponding to the infrared image in FIG. 5D, in accordance with at example embodiment.
Figure 7A:
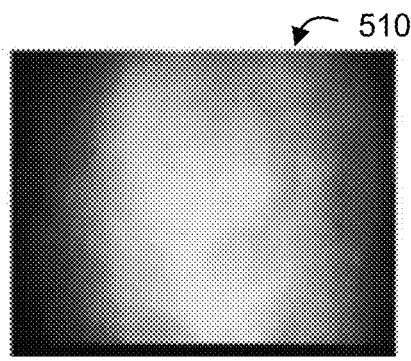
FIG. 7A is an infrared image of a side view of an individual's head when the individual is under no impairment, in accordance with an example embodiment.
Figure 7B:
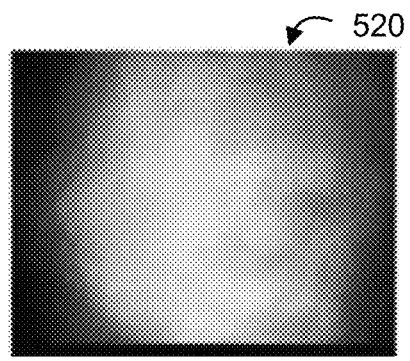
FIG. 7B shows the side view of the individual's head in FIG. 7A when the individual is under impairment, in accordance with an example embodiment.
Figure 7C:
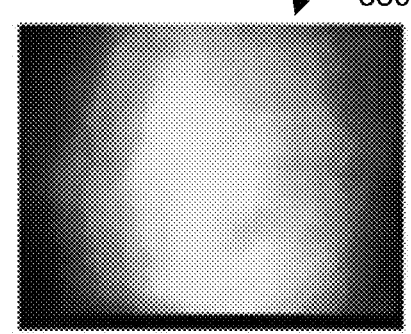
FIG. 7C shows the side view of the individual's head in FIGS. 7A and 7B when the individual is at another impairment level, in accordance with an example embodiment.
Figure 7D:
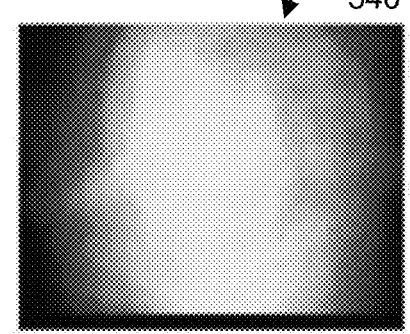
FIG. 7D shows the side view of the individual's head in FIGS. 7A to 7C when the individual is at another impairment level, in accordance with an example embodiment.
Figure 8A:
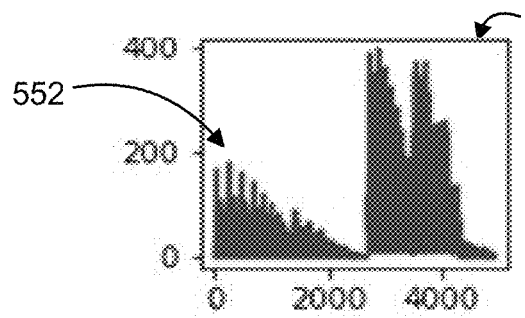
FIG. 8A is an example intensity representation corresponding to the infrared image in FIG. 7A, in accordance with at example embodiment.
Figure 8B:
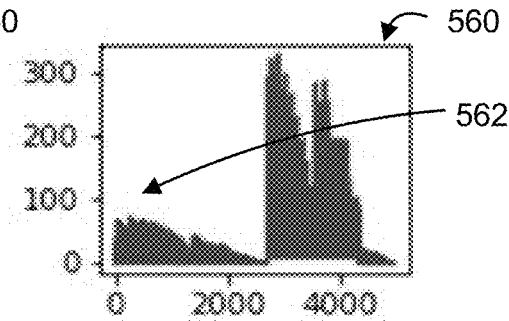
FIG. 8B is an example intensity representation corresponding to the infrared image in FIG. 7B, in accordance with at example embodiment.
Figure 8C:
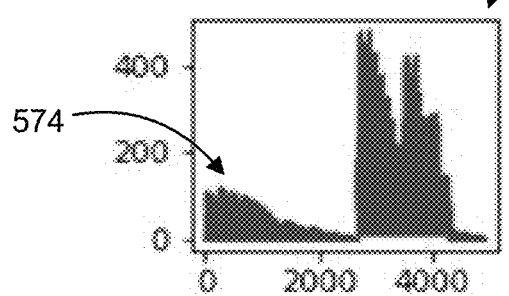
FIG. 8C is an example intensity representation corresponding to the infrared image in FIG. 7C, in accordance with at example embodiment.
Figure 8D:
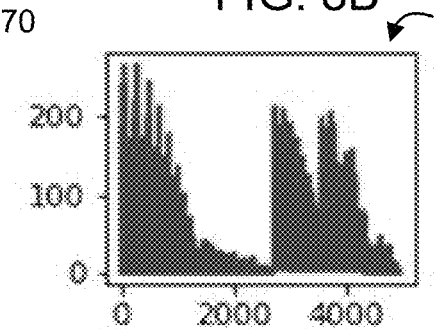
FIG. 8D is an example intensity representation corresponding to the infrared image in FIG. 7D, in accordance with at example embodiment.
Figure 9A:
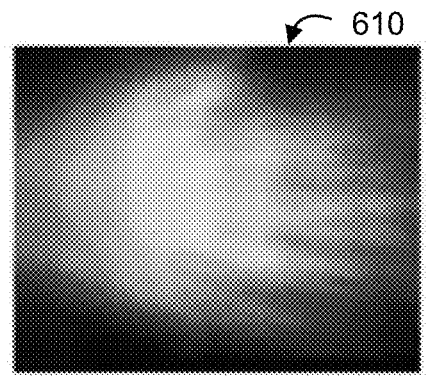
FIG. 9A is an infrared image of an individual's hand when the individual is under no impairment, in accordance with an example embodiment.
Figure 9B:
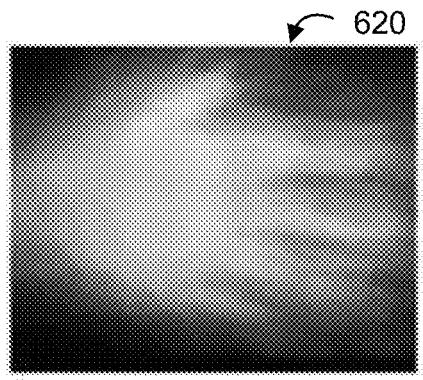
FIG. 9B shows the individual's hand in FIG. 9A when the individual is under impairment, in accordance with an example embodiment.
Figure 9C:
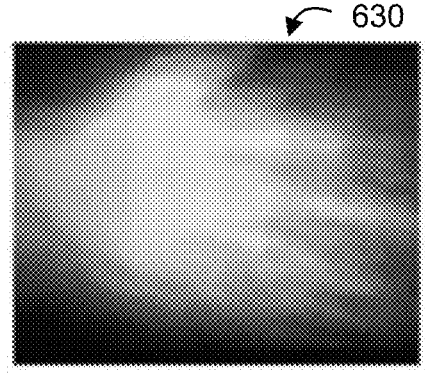
FIG. 9C shows the individual's hand in FIGS. 9A and 9B when the individual is at another impairment level, in accordance with an example embodiment.
Figure 9D:
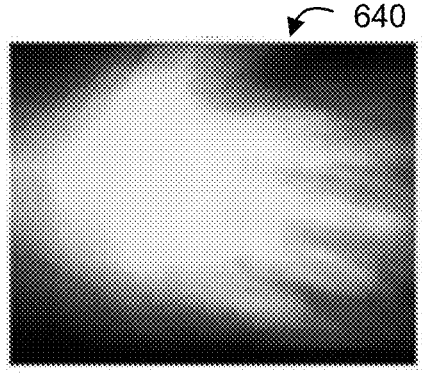
FIG. 9D shows the individual's hand in FIGS. 9A to 9C when the individual is at another impairment level, in accordance with an example embodiment.
Figure 10A:
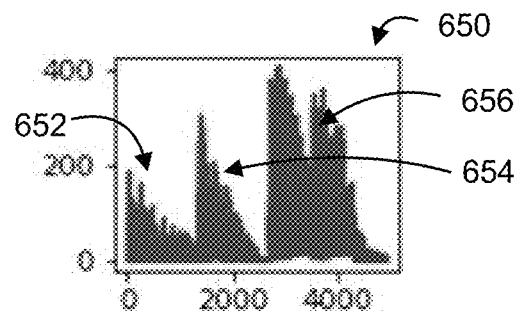
FIG. 10A is an example intensity representation corresponding to the infrared image in FIG. 9A, in accordance with at example embodiment.
Figure 10B:
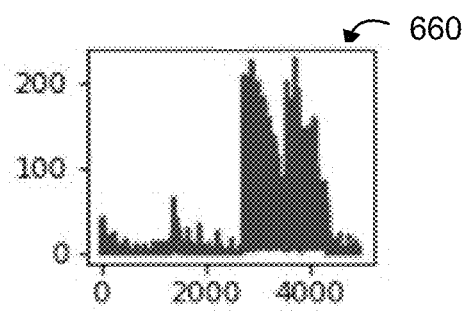
FIG. 10B is an example intensity representation corresponding to the infrared image in FIG. 9B, in accordance with at example embodiment.
Figure 10C:
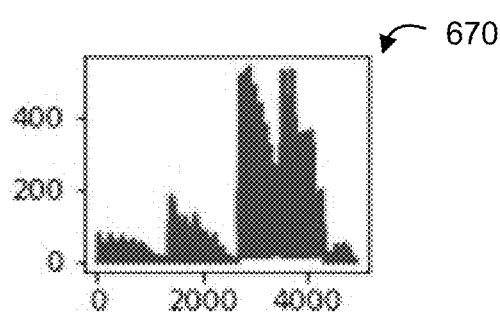
FIG. 10C is an example intensity representation corresponding to the infrared image in FIG. 9C, in accordance with at example embodiment.
Figure 10D:
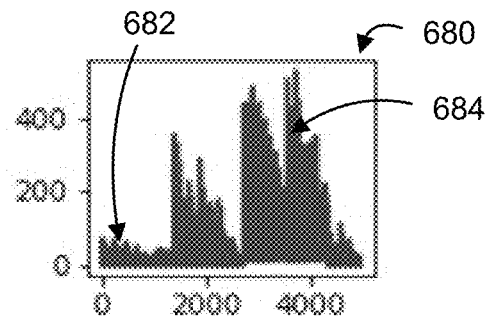
FIG. 10D is an example intensity representation corresponding to the infrared image in FIG. 9D, in accordance with at example embodiment.

Referring now to FIG. 2, shown therein is a flowchart illustrating an example method 200 of operating the impairment detection system 160 for detecting impairment of the individual 110. To illustrate the method 200, reference will be made to FIGS. 3 to 10.

At 210, the impairment detection system 160 receives at least one image associated with an individual.

For example, the image sensing device 120i can capture one or more images of the individual 110 and transmit the image(s) to the impairment detection system 160 via the network 130. In some embodiments, the impairment detection system 160 can receive the image(s) from the sensing device 120, data storage 150 and/or the computing device 140.

The image(s) can include an infrared image, in some embodiments. FIGS. 3A to 3D, 5A to 5D, 7A to 7D, and 9A to 9D show example infrared images 310 to 340, 410 to 440, 510 to 540, and 610 to 640, respectively. The images in FIGS. 3A to 3D, 5A to 5D, 7A to 7D, and 9A to 9D each show a different portion of the body of the individual 110.

FIGS. 3A to 3D show infrared images 310 to 340 of the eyes and nose of the individual 110 at different levels of impairment. Infrared image 310 corresponds to the individual when under no impairment, infrared images 320 and 330 correspond to the individual when under mild impairment, and infrared image 340 corresponds to the individual when under severe impairment.

FIGS. 5A to 5D show infrared images 410 to 440 of the front view of the head of the individual 110 at different levels of impairment. Infrared image 410 corresponds to the individual when under no impairment, infrared images 420 and 430 correspond to the individual when under mild impairment, and infrared image 440 corresponds to the individual when under severe impairment.

FIGS. 7A to 7D show infrared images 510 to 540 of a side view of the head, including the ear of the individual 110 at different levels of impairment. Infrared image 510 corresponds to the individual when under no impairment, infrared images 520 and 530 correspond to the individual when under mild impairment, and infrared image 540 corresponds to the individual when under severe impairment.

FIGS. 9A to 9D show infrared images 610 to 640 of a hand of the individual 110 at different levels of impairment. Infrared image 610 corresponds to the individual when under no impairment, infrared images 620 and 630 correspond to the individual when under mild impairment, and infrared image 640 corresponds to the individual when under severe impairment.

In some embodiments, the impairment detection system 160 can receive two or more images associated with the individual 110. For example, the impairment detection system 160 may receive a first image and a second image associated with the individual 110. The first image may depict a portion of the individual 110 that is different than depicted in the second image—that is, the first image can include image 310 (which relates to the individual's 110 eyes and nose) and the second image can include image 410 (which relates to the head). In some embodiments, the first image can depict a first view of a portion of the individual 110 and the second image can depict a second view of that portion. For example, the first image can be a front view of the head, and the second image can be a side view of the head.

Continuing with reference to FIG. 2, in an example embodiment, the impairment detection system 160 can receive images 340, 440, 540 and 640, which correspond to the individual 110.

At 220, the impairment detection system 160 identifies at least one feature in each image.

The feature identified by the impairment detection system 160 in each image relates to a property or characteristic identifiable in the image. For example, the feature can relate to an intensity distribution within an image, and/or a region of interest.

For example, the impairment detection system 160 can apply feature analytical models to the image for identifying the region of interest, such as a portion of a body of the individual 110. One or more feature analytical models relating to different body parts can be stored in the data storage 150, 166. To identify the one or more body parts to which each image relates, the impairment detection system 160 can apply the feature analytical models to determine which body part has the highest associated confidence level. To assist with the feature analytical models, the impairment detection system 160 can apply different image analysis techniques to the image, such as image preprocessing to enhance relevant pixel information, for example, and/or image segmentation to focus on the regions of interest.

In some embodiments, the impairment detection system 160 can preprocess the image to assist with identifying of the feature(s). For example, the impairment detection system 160 may perform scaling, rotation, grey-scaling, cropping, or any other suitable method on the image. In some embodiments, the preprocessing can normalize image data to modify images with different ranges of intensities to be consistent. The impairment detection system 160 can also reduce noise in the image data to improve detection accuracy.

The impairment detection system 160 can also generate the feature analytical models based on a set of feature training images associated with a plurality of individuals. For example, the impairment detection system 160 can generate the feature analytical models using convolutional neural networks (CNNs). Each training image can be associated, or labelled or tagged, with one or more features, and the impairment detection system 160 can analyze each labelled training image, or the specific region of interest, to develop the feature analytical model for that associated feature. The impairment detection system 160 can store the feature analytical model in the data storage 150, 166, and can continue to update the feature analytical model with new training data, in some embodiments.

For example, when the impairment detection system 160 receives images 340, 440, 540 and 640, the impairment detection system 160 can identify the feature(s) represented in images 340, 440, 540 and 640 by applying the feature analytical models stored in the data storage 150, 166. From applying the feature analytical models to the image 340, the impairment detection system 160 can determine that the image 340 is more likely related to the eyes and nose of an individual. Similarly, when the impairment detection system 160 applies the feature analytical models to the images 440, 540 and 640, the impairment detection system 160 can determine that the images 440, 540 and 640 are more likely related to the front view of a head of an individual, the side view of a head of an individual, and the hand of the individual.

In some embodiments, the impairment detection system 160 can apply various pattern recognition algorithms to automatically identify the features represented by the image 340. Example pattern recognition algorithms can include, but are not limited to techniques based on histograms of gradient, Haar-like features, local binary patterns, and/or Haralick features. For example, the impairment detection system 160 can generate a pattern from the image using local binary pattern. The features extracted by the local binary pattern can be stored in feature vectors, which may be normalized in some embodiments.

In some embodiments, the impairment detection system 160 can extract a portion of the image data for analysis. For example, the impairment detection system 160 can extract the portion of the image data related to the individual. An example image can include multiple individuals in a motor vehicle. The impairment detection system 160 can extract the portion of the image that is associated with the driver of the motor vehicle for analysis. The impairment detection system 160 can then proceed to identify the feature associated with the portion of image data.

At 230, the impairment detection system 160 generates an intensity representation for each feature identified at 220.

The intensity representation can represent the intensity at each pixel of the image. For infrared images, such as 310 to 340, 410 to 440, 510 to 540, and 610 to 640, each pixel is associated with a heat intensity of the individual. The heat intensity displayed by the individual 110 can vary with the impairment level due changes in blood flow or blood pressure resulting from the impairing substance. For the purpose of illustration, FIGS. 4A to 4D, 6A to 6D, 8A to 8D, and 10A to 10D show example intensity representations 350 to 380, 450 to 480, 550 to 580, and 650 to 680, respectively. Example intensity representations 350 to 380, 450 to 480, 550 to 580, and 650 to 680 are histograms that illustrate a frequency of a pixel intensity within the corresponding infrared image 310 to 340, 410 to 440, 510 to 540, and 610 to 640. Other forms of intensity representations can be used and in some embodiments, the methods and systems disclosed herein may not graphically display the intensity representations.

FIGS. 4A to 4D are intensity representations 350 to 380 that correspond to the infrared images 310 to 340 of FIGS. 3A to 3D, respectively. FIGS. 6A to 6D are intensity representations 450 to 480 that correspond to the infrared images 410 to 440 of FIGS. 5A to 5D, respectively. As shown from the intensity representations 350 to 380 and 450 to 480, the variability in the heat distribution in the eyes and nose, and front view of the head at the different impairment levels are not as visually discernible. However, visual discernibility is insignificant to the impairment analytical models.

FIGS. 8A to 8D are intensity representations 550 to 580 that correspond to the infrared images 510 to 540 of FIGS. 7A to 7D, respectively. Intensity representation 550 corresponds to the infrared image 510, which is associated with no impairment; intensity representations 560 and 570 correspond to the infrared images 520 and 530, which are associated with mild impairment; and intensity representation 580 corresponds to the infrared image 540, which is associated with severe impairment. As can be seen generally at 552 in the intensity representation 550, there is greater variability in the pixel intensity at the lower end for the image 510 associated with no impairment. For mild impairment, as shown generally at 562 and 574, there is less variability in the pixel intensity at the lower end for images 520 and 530. For severe impairment, as can be seen from the intensity representation 580, there is less variability in the overall intensity distribution.

FIGS. 10A to 10D are intensity representations 650 to 680 that correspond to the infrared images 610 to 640 of FIGS. 9A to 9D, respectively. Intensity representation 650 corresponds to the infrared image 610, which is associated with no impairment; intensity representations 660 and 670 correspond to the infrared images 620 and 630, which are associated with mild impairment; and intensity representation 680 corresponds to the infrared image 640, which is associated with severe impairment. As shown generally at 652, 654 and 656 of the intensity representation 650, the infrared image 610 has a great variability in intensity throughout. That is, the hand of an individual under no impairment has a more variable heat distribution. In contrast, the intensity representations 660 and 670 have less variability in contrast with the intensity representation 650. For the hand of an individual under severe impairment, as illustrated by the intensity representation 680, the higher intensity region (generally shown at 684) is denser than the lower intensity region (generally shown at 682).

In some embodiments, the impairment detection system 160 can generate the intensity representation for a portion of the image. For example, the impairment detection system 160 may generate a histogram to represent intensity values of only a particular portion of the image identified to be of interest.

At 240, the impairment detection system 160 applies at least one impairment analytical model to the intensity representation to determine a respective impairment likelihood.

Continuing with the example with receiving images 340, 440, 540 and 640, the impairment detection system 160 can generate the corresponding intensity representations 380, 480, 580 and 680 (at 230). The impairment detection system 160 can then apply an impairment analytical model to each intensity representation 380, 480, 580 and 680 to determine an impairment likelihood.

The impairment analytical models relate features identified within each intensity representation and/or images to an impairment level. Different impairment analytical models can be developed for different features. For example, an impairment analytical model can be developed for images related to the side profile of the head that are associated with severe impairment, and another impairment analytical model can be developed for images related to the side profile of the head that are associated with no impairment. An impairment analytical model can be developed for images related to the hand associated with severe impairment and another impairment analytical model can be developed for images related to the hand associated with no impairment.

In some embodiments, the impairment detection system 160 can develop impairment analytical models only for images associated with no impairment, or for images associated with impairment. Any images that do not fit well within the resulting impairment analytical model associated with no impairment can be determined to be impaired, and vice versa.

When the impairment detection system 160 applies the impairment analytical model to each intensity representation 380, 480, 580 and 680, the impairment detection system 160 can determine how closely the features corresponding to the intensity representation 380, 480, 580 and 680 align with the features represented by the impairment analytical model. For example, the impairment likelihood can correspond to a numerical value (e.g., a percentage) indicating how well each intensity representation 380, 480, 580 and 680 fits with respect to the applied impairment analytical model. In some embodiments, the impairment detection system 160 can generate a binary determination for the impairment likelihood—that is, the intensity representation 380, 480, 580 and 680 fits or does not fit.

In some embodiments, the impairment detection system 160 can generate the impairment analytical model based on a set of impairment training images. The set of impairment training images can be stored in the data storage 150, 166. The set of impairment training images can include one or more images associated with different individuals, and each image can be associated with an impairment level. The impairment detection system 160 can then generate the impairment analytical model based on the set of impairment training images and the impairment level associated with each impairment training image. For example, the impairment detection system 160 can generate the impairment analytical model by applying a pattern recognition algorithm to the set of impairment training images and the one or more associated impairment levels to establish patterns and/or relationship between the features identified in the training images and the associated impairment levels. In some embodiments, multiple pattern recognition algorithms can be applied.

Example pattern recognition algorithms can include, but are not limited to, techniques based on nearest neighbor, k-nearest neighbors, support vector machines, naive Bayesian, decision trees, random forests, logistic regression, and/or linear discriminant analysis. With each pattern recognition algorithm, different aspects of the intensity representation can be analyzed. For example, the impairment detection system 160 can apply the logistic regression technique to establish linear relationships between the identified features, whereas the impairment detection system 160 can apply the random forest technique to develop a set of rules based on the identified features.

At 250, the impairment detection system 160 determines a confidence level for each impairment likelihood based on characteristics associated with at least the applied impairment analytical model and the associated feature.

The resulting impairment defined by the impairment detection system 160 can vary with the type of data received by the impairment detection system 160 and/or impairment analytical model used. For example, certain sources and/or quality of data can be more dependable than others, and certain impairment analytical models can be reliable than others in certain environments. The impairment detection system 160 can generate the confidence level to reflect these variables.

For example, the impairment detection system 160 can consider the image quality of the image. When the image quality of the image satisfies a quality threshold, the impairment detection system 160 can generate a quality indicator to indicate that the image quality satisfies the quality threshold and can have a positive effect on the confidence level. The quality threshold can indicate a minimal resolution required for the image quality to be satisfactory.

The impairment detection system 160 may also consider the view or perspective of the image when defining the impairment of the individual 110. For example, the impairment detection system 160 may determine that the image 440 related to the front view of the head to be less reliable than the image 540, which is of the side view of the head. The image reliability indicator can vary depending on which view is provided. The image reliability indicator can be a binary value ('0' for low reliability and '1' for high reliability) or a numerical value. The impairment detection system 160 can then factor the image reliability indicator when determining the confidence level for each impairment likelihood.

In some embodiments, the impairment detection system 160 can consider the type of feature when defining the impairment of the individual 110. For example, as illustrated with the intensity representation 580 associated with the side profile of the head and the intensity representation 380 associated with the eyes and nose, the side profile of the head can provide more valuable information. The impairment detection system 160 can assign a higher feature reliability indicator to the intensity representation 580 than for intensity representation 380, for example. The feature reliability indicator can be a binary value ('0' for low reliability and '1' for high reliability) or a numerical value. The impairment detection system 160 can then determine the confidence level for each impairment likelihood based on the feature reliability indicator.

The impairment detection system 160 may consider the type of impairment analytical model used. Certain impairment analytical models may be more appropriate for certain features and so, may not be as reliable in some situations. Some analytical models may also be generated from a very small set of training dataset and so, may be less sophisticated. The impairment detection system 160 can assign a model reliability indicator to each impairment analytical model and vary the confidence level for each impairment likelihood based on the model reliability indicator. The model reliability indicator can be a binary value ('0' for low reliability and '1' for high reliability) or a numerical value.

Steps 230, 240, and 250 can be repeated by the impairment detection system 160 for each feature in each image identified at 220.

At 260, the impairment detection system 160 defines the impairment of the individual 110 based on at least one impairment likelihood and the respective confidence level.

The impairment level of the individual 110 can be represented by an impairment indicator indicating how impaired that individual is. For example, the impairment indicator can be a text indicator, such as "impaired", "likely impaired", or "not impaired", or a numerical indicator, such as a number between 0 and 100, where 0 represents minimal impairment and 100 represents high impairment.

The impairment detection system 160 can define the impairment of the individual by taking an average of each impairment likelihood weighted by the respective confidence level. In some embodiments, the impairment detection system 160 can determine the impairment likelihood based on majority voting so that if a majority of the impairment likelihood indicates impaired, then the impairment detection system 160 will define the impairment of the individual 110 to be impaired.

In some embodiments, the impairment detection system 160 can exclude some of the impairment likelihoods. For example, the impairment detection system 160 can determine whether a confidence level associated with an impairment likelihood satisfies a confidence threshold. The confidence threshold corresponds to a minimum confidence level necessary to affect the impairment of the individual 110. When the impairment detection system 160 determines that the confidence threshold is not satisfied, the impairment detection system 160 can eliminate that impairment likelihood from affecting the impairment definition at 260.

In contrast, the impairment detection system 160 can determine that the individual 110 is impaired when an impairment threshold is satisfied by one of the impairment likelihoods (or an impairment likelihood weighted by the corresponding confidence level). The impairment threshold corresponds to a minimum impairment likelihood that would trigger a definitive impairment determination.

There can also be embodiments in which the impairment detection system 160 can determine different levels of impairments. The impairment detection system 160 can determine whether the impairment likelihood (or an impairment likelihood weighted by the corresponding confidence level) satisfies a first impairment threshold. The first impairment threshold is the minimum impairment likelihood necessary to trigger a first impairment level (e.g., "severe impairment"). When the impairment detection system 160 determines that the first impairment threshold is satisfied, the impairment detection system 160 can define the impairment to be severe. However, if the impairment detection system 160 determines that the first impairment threshold is not satisfied, the impairment detection system 160 can determine whether the impairment likelihood (or the impairment likelihood weighted by the corresponding confidence level) satisfies a second impairment threshold lower than the first impairment threshold. The second impairment threshold is the minimum impairment likelihood necessary to trigger a second impairment level (e.g., "mild impairment"). When the impairment detection system 160 determines that the second impairment threshold is satisfied, the impairment detection system 160 can define the impairment to be mild. Otherwise, the impairment detection system 160 can generate the impairment indicator as not impaired.

Depending on the application of the impairment detection system 160, the impairment detection system 160 can, in some embodiments, generate the impairment indicator to indicate that the individual 110 is impaired by *cannabis*.

In embodiments where the impairment detection system 160 receives two or more images, the impairment detection system 160 can generate an impairment indicator indicating an impairment level of the individual based on the at least one impairment likelihood and the respective confidence level associated with each image of the two or more images.

In some embodiments, the impairment detection system 160 can determine the impairment of the individual 110 also using an audio recording involving the individual 110. The impairment likelihood determined for the audio recording can be applied to the impairment definition at 260. For example, the impairment detection system 160 can receive the audio recording and identify an audio property associated with the audio recording. The audio property can relate to various aspects of the audio recording, such as the amplitude, pitch, loudness, or jitteriness. The impairment detection system 160 can then apply the audio analytical model related to the identified audio property to the audio recording to determine an impairment likelihood. The impairment detection system 160 can generate a confidence level for the impairment likelihood based on different characteristics of the audio analytical model and the audio property, as well. For ease of exposition, the determination of impairment based on the audio recording will now be described with reference to FIGS. 11 to 13.

Figure 11:
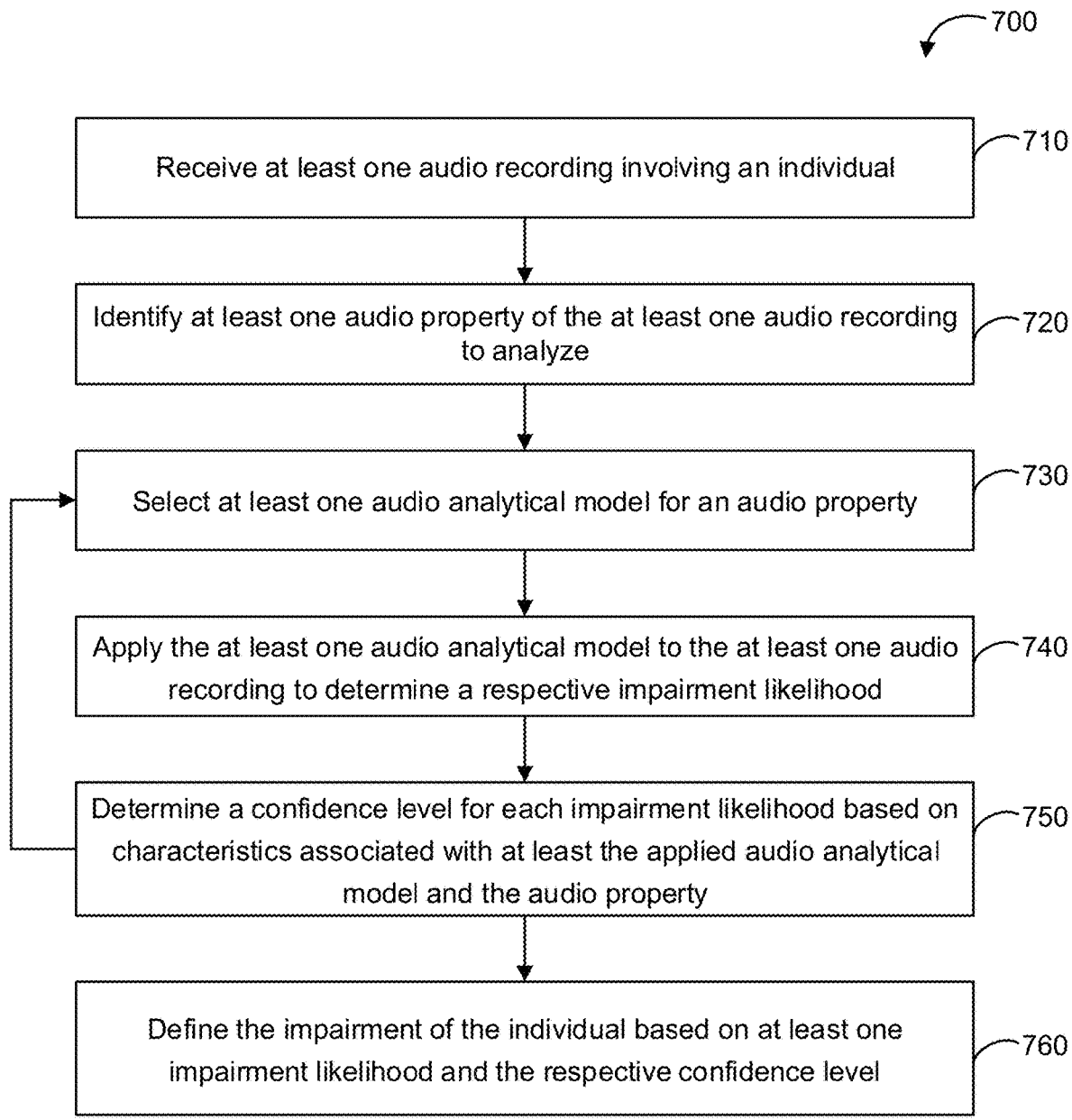
FIG. 11 is a flowchart of another example method of operating the impairment detection system for detecting impairment of the individual.

Reference will now be made to FIG. 11, which illustrates an example method 700 of operating the impairment detection system 160 for determining impairment of the individual 110. To illustrate the method 700, reference will be made to FIGS. 12 and 13.

At 710, the impairment detection system 160 receives at least one audio recording involving the individual 110. The audio recording can include audio data of only the individual 110 or multiple individuals, including the individual 110. When the impairment detection system 160 determine that multiple individuals are involved in the audio recording, the impairment detection system 160 can apply voice recognition to the audio recording to identify the segments or frames in which the individual 110 of interest is the predominant speaker.

At 720, the impairment detection system 160 identifies at least one audio property of the at least one audio recording to analyze.

Different properties of audio data can be analyzed for facilitating the determination of impairment of the individual 110. Example properties can include, but are not limited to, loudness, jitteriness, and/or pitch. In some embodiments the impairment detection system 160 can identify various spectral features, such as spectral centroid to represent a center of mass of a spectrum (e.g., based on various different methods such as linear, logarithmic or exponential power of the spectrum); spectral flatness (typically measured in decibels) to represent how similar the audio is to noise, as opposed to tone, spectral complexity to represent a number of peaks in the spectrum; spectral contrast to represent aspects of the spectral peak, spectral valley, and the difference between the spectral peak and valley in each frequency subband; spectral roll-off to represent an amount of the right-skewedness of the spectrum; and spectral flux to represent how quickly a power spectrum of an audio signal is changing. The spectral flux can, in some embodiments, be determined by comparing the power spectrum for one frame against the power spectrum from a previous frame.

In some embodiments, the impairment detection system 160 can derive mel-frequency cepstral coefficients (MFCCs), Bark-frequency cepstral coefficients (BFCCs), and/or gammatone frequency cepstral coefficients (GFCCs) from a type of cepstral representation of the audio clip. Mel-frequency cepstral coefficients can involve filters with center frequencies that are spaced along the mel scale, bark-frequency cepstral coefficients can involve filters with center frequencies spaced along the bark scale, and gammatone frequency cepstral coefficients can involve filters with center frequencies along the gammatone scale.

In some embodiments, the impairment detection system 160 can determine linear predictive coefficients (LPCs) and associated reflection coefficients of a signal; energies or magnitudes in equivalent rectangular bandwidth (ERB) bands of a spectrum using an equivalent rectangular bandwidth scale, for example; a sensory dissonance of an audio signal based on a roughness of the spectral peaks of the audio signal to represent a perceptual roughness of the sound; a ratio between the odd and even harmonic energy of a signal, with respect to the harmonic peaks of the signal; and tristimulus values of the audio signal with respect to its harmonic peaks to represent a mixture of the harmonics in a sound. Different variations of the tristimulus values can be used, such as a tristimulus value that represents a relative weight of the first harmonic, a tristimulus value that represents a relative weight of the second, third, and fourth harmonics; and a tristimulus value that represents the relative weight of all the remaining harmonics.

In some embodiments the impairment detection system 160 can determine a mean and standard deviation of the fundamental frequency (FOHz); a Harmonics-to-Noise (HNR) ratio to represent a measure of the proportion of harmonic sound to noise in the voice measured in decibels; mean and median of formants, which correspond to a concentration of acoustic energy around a particular frequency in the speech wave; average absolute difference between consecutive periods, divided by the average period; average absolute difference between consecutive periods (which can be represented in seconds); a relative average perturbation to represent an average absolute difference between a period and the average of it and its two neighbours, divided by the average period; a five-point period perturbation quotient to represent an average absolute difference between a period and the average of it and its four closest neighbours, divided by the average period; an average absolute difference between consecutive differences between consecutive periods, divided by the average period; an average absolute difference between the amplitudes of consecutive periods, divided by the average amplitude; an average absolute base-10 logarithm of the difference between the amplitudes of consecutive periods, multiplied by 20; a three-point amplitude perturbation quotient to represent the average absolute difference between the amplitude of a period and the average of the amplitudes of its neighbours, divided by the average amplitude; a five-point amplitude perturbation quotient to represent the average absolute difference between the amplitude of a period and the average of the amplitudes of it and its four closest neighbours, divided by the average amplitude; a 1-point amplitude perturbation quotient to represent an average absolute difference between the amplitude of a period and the average of the amplitudes of it and its ten closest neighbours, divided by the average amplitude; and an average absolute difference between consecutive differences between the amplitudes of consecutive periods. There can be different formants at a different frequency (e.g., a formant can be at each 1000 Hz band).

The impairment detection system 160 can identify a property that relates to the entire audio recording, such as the fundamental frequency for the entire audio recording, or a property related to a segment or frame of the audio recording. For example, the audio property may be an average loudness for a particular segment of the audio recording in which the individual 110 is speaking.

Figure 12:
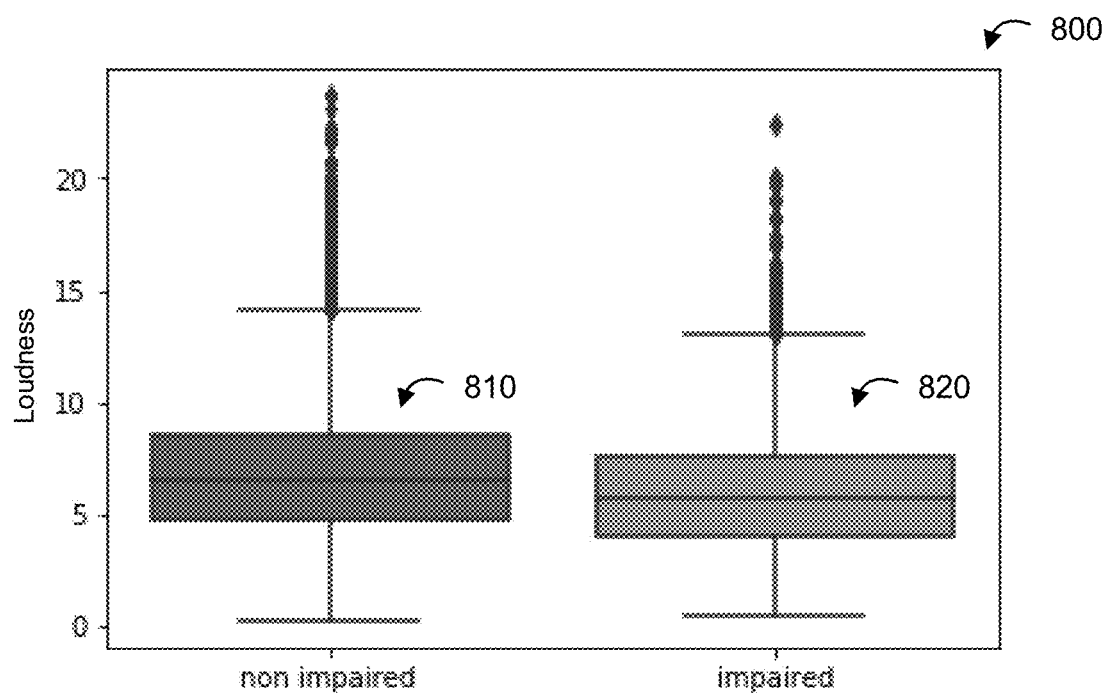
FIG. 12 is an example graphical representation illustrating an example audio property associated with different impairment levels, in accordance with an example embodiment.
Figure 13:
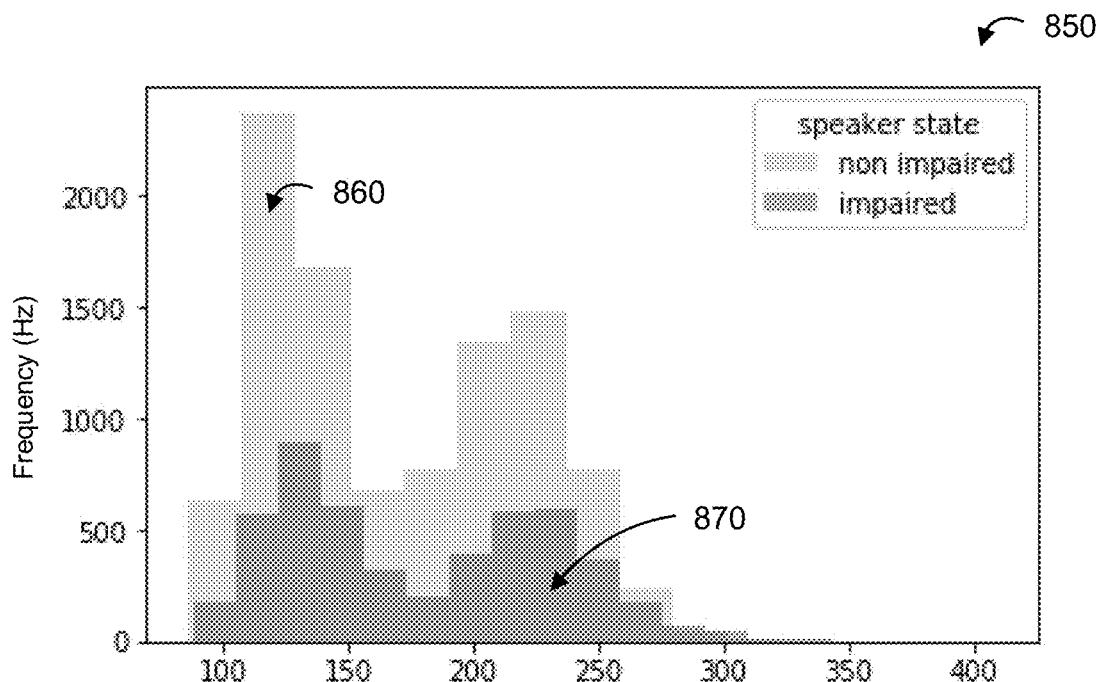
FIG. 13 is an example intensity representation illustrating another example audio property associated with different impairment levels, in accordance with an example embodiment.

FIG. 12 is a graph 800 illustrating loudness of not impaired speakers (at 810) and impaired speakers (at 820). FIG. 13 is a graph 850 illustrating a mean fundamental frequency of not impaired speakers (at 860) and impaired speakers (at 870). It can be difficult to visually determine from FIG. 12 the difference between the different speakers in terms of loudness. In FIG. 13, it can be seen that the fundamental frequency of an impaired speaker is less variable than a not impaired speaker.

In some embodiments, the impairment detection system 160 can preprocess the audio recording. For example, the impairment detection system 160 may remove portions of the audio recording associated with no or minimal speech. In some embodiments, the impairment detection system 160 may adjust the voice recording to enhance the audio properties, such as the equalization, volume, sampling rate, balance, and/or tone.

At 730, the impairment detection system 160 selects at least one audio analytical model for the audio property.

The audio analytical models relate features identified within each audio recording to an impairment level. Different impairment analytical models can be developed for different audio properties. For example, an audio analytical model can be developed for the audio property, loudness, related to those under severe impairment, and another audio analytical model can be developed for those under no impairment. In some embodiments, the impairment detection system 160 can develop audio analytical models for each property when under no impairment. Any audio recording that does not fit well within the resulting audio analytical model associated with no impairment can be determined to be impaired, and vice versa.

In some embodiments, the impairment detection system 160 can generate the audio analytical model based on a set of training audio recordings. The training audio recordings can be stored in the data storage 150, 166. The set of training audio recordings can include one or more audio recordings associated with different individuals, and each audio recording can be associated with an impairment level. The impairment detection system 160 can then generate the audio analytical model based on the training audio recordings and the impairment level associated with each training audio recording. For example, the impairment detection system 160 can generate the audio analytical model by applying a pattern recognition algorithm to the set of training audio recordings and the one or more associated impairment levels to establish patterns and/or relationship between the features identified in the training audio recordings and the associated impairment levels. In some embodiments, multiple pattern recognition algorithms can be applied.

Example pattern recognition algorithms can include, but are not limited to, techniques based on nearest neighbor, k-nearest neighbors, support vector machines, naive Bayesian, decision trees, random forests, logistic regression, gradient boosting algorithms (e.g., XGBoost), and/or linear discriminant analysis.

At 740, the impairment detection system 160 applies the at least one audio analytical model to the audio recording to determine a respective impairment likelihood of the individual. The audio analytical model can generate an impairment likelihood for the audio property based on how well certain properties of the audio recording fit with the audio analytical model.

At 750, the impairment detection system 160 determines the confidence level for each impairment likelihood based on characteristics associated with at least the audio analytical model and the audio property. As described with respect to 250, the impairment detection system 160 can determine that aspects of the audio recording and the analytical model can affect the reliability of the resulting impairment likelihood. The impairment detection system 160 can then adjust the confidence level accordingly.

Steps 730, 740, and 750 can be repeated by the impairment detection system 160 for each audio property of the audio recording identified at 720.

At 760, the impairment detection system 160 defines the impairment of the individual based on at least one impairment likelihood and the respective confidence level. Similar to 260, the impairment detection system 160 can define the impairment of the individual 110 based on various methods and factors. Based on the determination, the impairment detection system 160 can generate the impairment indicator to represent the impairment level accordingly.

Figure 14:
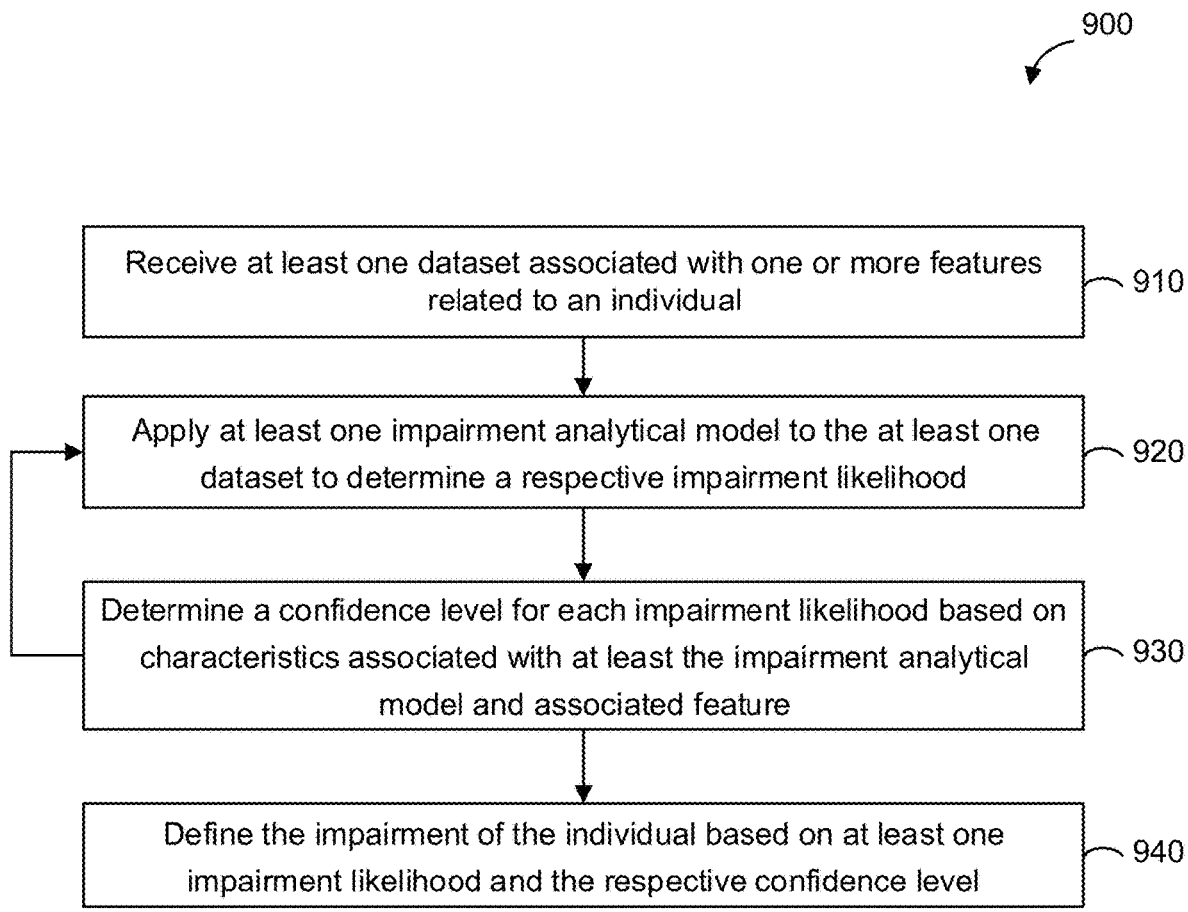
FIG. 14 is a flowchart of another example method of operating the impairment detection system for detecting impairment of the individual.

Referring now to FIG. 14, shown therein is a flowchart illustrating an example method 1200 of operating the impairment detection system 160 for detecting impairment of the individual 110.

At 1210, the impairment detection system 160 receives at least one dataset associated with one or more features related to the individual 110.

The dataset can include data associated with more than one feature related to the individual 110. For example, the dataset can include physiological and/or vital sign measurements of the individual 110, such as, but not limited to, a brain wave recording, a heart rate recording, hydration levels, and/or an electrocardiogram (ECG) recording. The dataset can also include other data, such as images, videos, and/or audio recordings involving the individual 110. The impairment detection system 160 can consider multiple different types of data when determining the impairment of the individual. For example, and not of limitation, the impairment detection system 160 can the impairment of the individual based on the hydration level, the body temperature and/or the electrocardiogram recording.

The impairment detection system 160 can receive the data from one or more of the sensing devices 120 and/or the computing device 140, and/or from the data storage 150, 166.

At 1220, the impairment detection system 160 applies at least one impairment analytical model to the dataset to determine a respective impairment likelihood. Analytical models represent relationships and patterns between variables using existing data. Analytical models can evolve as new data becomes available. The impairment analytical models applied herein by the impairment detection system 160 can determine an impairment likelihood for the dataset by determining how well the dataset fits within the analytical model. For each feature related to the individual 110, the impairment detection system 160 can apply an impairment analytical model to the corresponding data in the dataset.

For example, for a dataset that includes an image, the impairment detection system 160 can identify the feature(s) shown by the image. The impairment detection system 160 can apply one or more feature analytical models to the image to identify the illustrated feature(s). The impairment detection system 160 can also conduct image segmentation to the images to enhance the features being analyzed. After identifying the feature(s) shown by the image, the impairment detection system 160 can then apply the impairment analytical model for that feature for determining an impairment likelihood.

For a dataset that includes an audio recording, the impairment detection system 160 can apply an impairment analytical model related to the loudness, jitteriness, and/or pitch of the audio recording for determining the impairment likelihood.

For a dataset that includes a brainwave recording, the impairment detection system 160 can apply an impairment analytical model related to various aspects of the brainwave, such as the amplitude, frequency and/or pattern over a period of time. For a dataset that includes heart rate measurements, the impairment detection system 160 can apply an impairment analytical model related to various aspects of the heartbeat, such as the frequency, amplitude, and/or pattern. For a dataset that includes hydration levels, the impairment detection system 160 can apply an impairment analytical model related to the hydration levels. For a dataset that includes an electrocardiogram recording, the impairment detection system 160 can apply an impairment analytical model related to the amplitude, frequency and/or pattern over a period of time of the electrocardiogram and/or blood pressure.

In some embodiments, the impairment detection system 160 can receive a dataset that illustrates one or more features over a period of time. The impairment detection system 160 can then apply the relevant impairment analytical models to each set of data to determine a change in the feature over the period of time, and determine any differences in the impairment level. For example, for an image, the impairment detection system 160 may analyze the movement of a body part, such as an eye or pupil, over the period of time. In some embodiments, the impairment detection system 160 may identify anomalies in the features.

In some embodiments, the impairment detection system 160 can also generate the impairment analytical models. To generate the analytical model for a feature, the impairment detection system 160 can receive a set of impairment training data related to that feature. The set of impairment training data includes known data from which patterns between the data and the impairment likelihood can be extrapolated by the impairment detection system 160. The set of impairment training data can include data related to a wide spectrum of individuals—that is, individuals of different genders, ages, ethnicities, and/or in different surroundings. The impairment detection system 160 can associate each impairment training data with an impairment indicator, and store the associated impairment indicator with that impairment training data in the data storage 150, 166. The impairment indicator can indicate an impairment level.

Based on the set of impairment training data and the impairment indicator associated with each impairment training data, the impairment detection system 160 can then generate the impairment analytical model for that feature by extrapolating patterns within each training data and the associated impairment likelihood.

The impairment analytical models can be generated using various regression and machine learning techniques, such as, but not limited to, nearest neighbor, k-nearest neighbors, support vector machines, naive Bayesian, decision trees, random forests, logistic regression, and/or linear discriminant analysis. It will be appreciated that other techniques can be used to generate the analytical models, including, but not limited to, classification, dimensionality reduction, gradient boosting, clustering, anomaly detection, pattern detection. In some embodiments, an impairment analytical model may be an ensemble model that is be generated using two or more different techniques.

At 1230, the impairment detection system 160 determines a confidence level for each impairment likelihood based on characteristics associated with at least the impairment analytical model and the associated feature.

Some impairment likelihoods may be less accurate or less reliable than other impairment likelihoods. For example, particular analytical models or particular properties may be less accurate predictors of impairment. Accordingly, the impairment detection system 160 can determine a confidence level for each impairment likelihood. Various techniques can be used by the impairment detection system 160 to determine a confidence level. For example, the impairment detection system 160 may consider the quality of a dataset, the type of dataset, the type of property, and the type of analytical model.

In some embodiments, the impairment detection system 160 may determine an accuracy associated with an analytical model and determine a confidence level based on the accuracy. For example, the impairment detection system 160 may receive a plurality of test datasets associated with a plurality of individuals. The impairment detection system 160 may also receive a plurality of impairment indicators. Each impairment indicator may indicate an impairment level of an individual associated with a test dataset. The impairment detection system 160 can then determine an accuracy associated with the analytical model by applying the analytical model to the plurality of test datasets and comparing the results with the plurality of impairment indicators. In some embodiments, the accuracy associated with an analytical model may be determined using a Leave One Out (LOO) approach.

The impairment detection system 160 can repeat steps 1220 and 1230 for each feature of the at least one dataset received at 1210.

At 1240, the impairment detection system 160 defines the impairment of the individual 110 based on at least one impairment likelihood and the respective confidence level.

The impairment detection system 160 may define the impairment of the individual 110 in various ways. For example, the impairment detection system 160 may determine whether the impairment likelihoods and respective confidence levels exceed a threshold and in the case that the impairment likelihood and confidence levels exceed the respective threshold, define the impairment as impaired, otherwise, not impaired. In another embodiment, the impairment detection system 160 can define the impairment of the individual 110 by applying a weighted average to the determined confidence levels, or with a voting algorithm. In some embodiments, the impairment detection system 160 may define an impairment indicator with a text indicator (e.g., "impaired", "likely impaired", "not impaired"), and/or a numerical indicator (e.g., a score from 0-100).

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements. Furthermore, the term "body" typically refers to the body of a patient, a subject or an individual who receives the ingestible device. The patient or subject is generally a human or other animal.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers (referred to herein as computing devices) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Various embodiments have been described herein by way of example only. Various modification and variations may be made to these example embodiments without departing from the spirit and scope of the invention, which is limited only by the appended claims.

We claim:

1. A method for detecting impairment of an individual, the method comprising operating a processor to:

receive at least two images associated with the individual, wherein a first image depicts a first portion of the individual and a second image depicts a second portion of the individual, the second portion of the individual being different from the first portion of the individual, and the first image being different from the second image;

identify at least one feature in each image of the at least two images, wherein the first image comprises a first feature type and the second image comprises a second feature type, the second feature type being different from the first feature type;

for each feature identified in each image:
generate an intensity representation for a region of that image associated with the feature, the intensity representation corresponding to a frequency distribution of pixel intensities for pixels in the region and each pixel in the region is associated with a heat intensity of the feature;
select at least one impairment analytical model related to the feature;
apply the at least one impairment analytical model to the intensity representation to determine a respective at least one impairment likelihood;
determine a feature reliability indicator for the feature, the feature reliability indicator representing a level of reliability of that feature for determining impairment of the individual;
determine a confidence level for each of the at least one impairment likelihood based on the feature reliability indicator and characteristics associated with the corresponding at least one impairment analytical model and that feature; and define the impairment of the individual based on the at least one impairment likelihood and the respective confidence level generated from the at least one feature in each image of the at least two images.

2. The method of claim 1, wherein determining the confidence level for each of the at least one impairment likelihood, based on the feature reliability indicator and the characteristics associated with the corresponding at least one impairment analytical model and the feature, comprises:
determining whether an image quality of the at least two images satisfies a quality threshold;
generating a quality indicator according to whether the image quality satisfies the quality threshold; and
determining the confidence level for each of the at least one impairment likelihood based at least on the quality indicator.

3. The method of claim 1, wherein determining the confidence level for each of the at least one impairment likelihood, based on the feature reliability indicator and the characteristics associated with the corresponding at least one impairment analytical model and the feature, comprises:
determining an image reliability indicator associated with an image view of the at least two images; and
determining the confidence level for each of the at least one impairment likelihood based at least on the image reliability indicator.

4. The method of claim 1, wherein determining the confidence level for each of the at least one impairment likelihood, based on the feature reliability indicator and the characteristics associated with the corresponding at least one impairment analytical model and the feature, comprises:
determining at least one model reliability indicator associated with the at least one impairment analytical model; and
determining the confidence level for each of the at least one impairment likelihood based at least on the at least one model reliability indicator.

5. The method of claim 1, further comprising operating the processor to:
receive at least one audio recording involving the individual;
identify at least one audio property of the at least one audio recording to analyze;
for each audio property:
select at least one audio analytical model for that audio property;
apply the at least one audio analytical model to the at least one audio recording to determine a respective impairment likelihood of the individual; and
determine the confidence level for each impairment likelihood based on characteristics associated with at least the applied audio analytical model and that audio property.

6. The method of claim 1, wherein defining the impairment of the individual comprises generating an impairment indicator indicating an impairment level of the individual based on the at least one impairment likelihood and the respective confidence level generated from the at least one feature in each image of the at least two images.

7. The method of claim 1, wherein receiving the at least two images associated with the individual comprises receiving:
the first image depicting a first view of a portion of the individual; and
the second image depicting a second view of the portion of the individual, the second view being different from the first view.

8. A system for detecting impairment of an individual, the system comprising:
a data storage to store one or more impairment analytical models; and
a processor operable to:
receive, via a network, at least two images associated with the individual, wherein a first image depicts a first portion of the individual and a second image depicts a second portion of the individual, the second portion of the individual being different from the first portion of the individual, and the first image being different from the second image;
identify at least one feature in each image of the at least two images, wherein the first image comprises a first feature type and the second image comprises a second feature type, the second feature type being different from the first feature type;
for each feature identified in each image:
generate an intensity representation for a region of that image associated with the feature, the intensity representation corresponding to a frequency distribution of pixel intensities for pixels in the region and each pixel in the region is associated with a heat intensity of the feature;
select at least one impairment analytical model related to the feature from the one or more impairment analytical models;
apply the at least one impairment analytical model the intensity representation to determine a respective at least one impairment likelihood;
determine a feature reliability indicator for the feature, the feature reliability indicator representing a level of reliability of that feature for determining impairment of the individual;

determine a confidence level for each of the at least one impairment likelihood based on the feature reliability indicator and characteristics associated with the corresponding at least one impairment analytical model and that feature; and define the impairment of the individual based on the at least one impairment likelihood and the respective confidence level generated from the at least one feature in each image of the at least two images.

9. The system of claim 8, wherein the processor is operable to:

determine whether an image quality of the at least two images satisfies a quality threshold;

generate a quality indicator according to whether the image quality satisfies the quality threshold; and determine the confidence level for each of the at least one impairment likelihood based at least on the quality indicator.

10. The system of claim 8, wherein the processor is operable to:

determine an image reliability indicator associated with an image view of the at least two images; and determine the confidence level for each of the at least one impairment likelihood based at least on the image reliability indicator.

11. The system of claim 8, wherein the processor is operable to:

determine a model reliability indicator associated with the at least one impairment analytical model; and determine the confidence level for each of the at least one impairment likelihood based at least on the model reliability indicator.

12. The system of claim 8, wherein the processor is operable to:

receive at least one audio recording involving the individual;

identify at least one audio property of the at least one audio recording to analyze;

for each audio property:
select at least one audio analytical model for that audio property;

apply the at least one audio analytical model to the at least one audio recording to determine a respective impairment likelihood of the individual; and determine the confidence level for each impairment likelihood based on characteristics associated with at least the applied audio analytical model and that audio property.

13. The system of claim 8, wherein the processor is operable to generate an impairment indicator indicating an impairment level of the individual based on the at least one impairment likelihood and the respective confidence level generated from the at least one feature in each image of the at least two images.

14. The system of claim 8, wherein the processor is operable to receive:

the first image depicting a first view of a portion of the individual; and the second image depicting a second view of the portion of the individual, the second view being different from the first view.

* * * * *